United States Patent [19]

Bixler et al.

[11] Patent Number: 5,785,973
[45] Date of Patent: Jul. 28, 1998

[54] SYNTHETIC PEPTIDES REPRESENTING A T-CELL EPITOPE AS A CARRIER MOLECULE FOR CONJUGATE VACCINES

[75] Inventors: Garvin Bixler, Fairport; Subramonia Pillai; Richard Insel, both of Rochester, all of N.Y.

[73] Assignee: Praxis Biologics, Inc., Rochester, N.Y.

[21] Appl. No.: 481,923

[22] Filed: Jun. 7, 1995

Related U.S. Application Data

[63] Continuation of Ser. No. 164,989, Dec. 9, 1993, abandoned, which is a continuation of Ser. No. 828,711, Jan. 31, 1992, abandoned, which is a continuation of Ser. No. 304,783, Jan. 31, 1989, abandoned, which is a continuation-in-part of Ser. No. 150,688, Feb. 1, 1988, abandoned.

[51] Int. Cl.$^6$ .......................... A61K 39/12; A61K 38/16; A61K 38/08

[52] U.S. Cl. ........................ 424/196.11; 424/194.1; 424/193.1; 424/186.1; 424/185.1; 424/184.1; 424/17; 514/13

[58] Field of Search .................... 424/197.11, 196.11, 424/194.1, 193.3, 190.1, 186.1, 185.1, 187.1, 184.1; 514/13, 17

[56] References Cited

U.S. PATENT DOCUMENTS

| | | | |
|---|---|---|---|
| 4,459,286 | 7/1984 | Hilleman et al. | 424/87 |
| 4,496,538 | 1/1985 | Gordon | 424/92 |
| 4,599,230 | 7/1986 | Milich et al. | 424/89 |
| 4,599,231 | 7/1986 | Milich et al. | 424/89 |
| 4,673,574 | 6/1987 | Anderson | 424/92 |
| 4,695,624 | 9/1987 | Marburg et al. | 530/395 |
| 4,711,779 | 12/1987 | Porro et al. | 424/92 |
| 4,722,840 | 2/1988 | Valenzuela et al. | 424/88 |
| 4,761,283 | 8/1988 | Anderson | 530/350 |
| 4,762,713 | 8/1988 | Anderson | 424/92 |
| 4,830,962 | 5/1989 | Gelfand et al. | 435/69.1 |
| 4,886,782 | 12/1989 | Good et al. | 530/324 |
| 4,902,506 | 2/1990 | Anderson et al. | 530/350 |
| 4,925,792 | 5/1990 | Rappuoli | 435/69.1 |
| 4,950,740 | 8/1990 | Greenfield et al. | 530/350 |

FOREIGN PATENT DOCUMENTS

| | | |
|---|---|---|
| 0172107 | 2/1986 | European Pat. Off. . |
| 0186576 | 7/1986 | European Pat. Off. . |
| 0245045 | 11/1987 | European Pat. Off. . |

OTHER PUBLICATIONS

Francis, Michael J. et al., "Non-responsiveness to a Foot-and-Mouth Disease Virus Peptide Overcome by Addition of Foreign Helper T-cell Determinants", *Nature*, 300;168-170 (Nov. 12, 1987).

Goebel, W.F., "Studies on Antibacterial Immunity Induced by Artificial Antigens," *Hospital of the Rockefeller Institute for Medical Research*, Dec. 1, 1938.

Maizels, R.M. et al., "Epitope Specificity of the T Cell proliferative Response to Lysozyme: Proliferative T Cells React Predominantly to Different Determinants From Those Recognized by B Cells," *Eur. J. Immunol.*, 10:509–515 (1980).

Schneerson, R., et al., "Preparation, Characterization, and Immunogenicity of *Haemophilus Influenzae* Type b Polysaccharide–Protein Conjugates," *J. of Experimental Medicine*, 152:361–376 (1980).

Kyte, J. and Doolittle, R.F., "A Simple Method for Displaying the Hydropathic Character of a Protein," *J. Mol. Biol.*, 157:105–132 (1982).

Jolivet, M., et al., "Epitope Specific Immunity Elicited by a synthetic Streptococcal Antigen Without Carrier or Adjuvant," *Biochem. and Biophysical Research Comm.*, 117(2):359–366 (1983).

Schutze, M–P., et al., "Carrier–Induced Epitopic Suppression, a Major Issue for Future Synthetic Vaccines," *J. of Immun.*, 135 94) :2319–2322 (1985).

Atassi, M.Z., et al., "Non–Specific Peptide Size Effects in the Recognition by Site–Specific T–Cell Clones," *Biochem. J.*, 246:307–312 91987).

Hopp, T.P. and Woods, K.R., "Prediction of Protein Antigenic Determinants from Amino Acid Sequences," *Proc. Natl. Acad. Sci. USA*, 78(6) :3824–3828 91981).

Watts, T.H., et al., "T–Cell Activation by Peptide Antigen: Effect of Peptide Sequence and Method of Antigen Presentation," *Proc. Natl. Acad. Sci. USA*, 82:5480–5484 (1985).

Good, M.F., et al., "Construction of Synthetic Immunogen: Use of New T–Helper Epitope on Malaria Circumsporozoite Protein," *Science*, 235:1059–1062 (1987).

Leclerc, C., et al., "A Synthetic Vaccine Constructed by Copolymerization of B and T Cell Determinants," *Eur. J. Immunol.*, 17:269–273 (1987).

Bixler, G.S., Jr. and Atassi, M.Z., "Molecular Localization of the Full Profile of the Continuous Regions Recognized by Myoglobin Primed T–Cells Using Synthetic Overlapping Peptides Encompassing the Entire Molecule," *Immunological Communications*, 12(6) :593–603 (1983).

DeLisi, c. and Berzofsky, J.A., "T–Cell Antigenic Sites Tend to be Amphipathic Structures," *Proc. Natl. Acad. Sci. USA*, 82:7048–7052 (1985).

Triebel, F., et al., "Immune Response to Diphtheria Toxin and to Different CNBr Fragments: Evidence for Different B and T Cell Reactivities," *Eur. J. Immunol.*, 16:47–53 (1986).

Geyer, H., et al., "Immunochemical Properties of Oligosaccharide–Protein Conjugates with Klebsiella–K2 Specificity," *Med. Microbiol. Immunol.*, 165:271–288 (1979).

(List continued on next page.)

*Primary Examiner*—Ponnathapura Achutamurthy
*Assistant Examiner*—T. D. Wessendorf
*Attorney, Agent, or Firm*—Hamilton, Brook, Smith & Reynolds, P.C.

[57] ABSTRACT

The present invention relates to novel T-cell epitopes of bacterial products. The epitopes of the invention may be employed in the preparation of conjugates between the epitopes and medically useful antigens, haptens, or antigenic determinants. These conjugates are capable of eliciting antibody responses similar to conjugates of antigens covalently coupled to carrier proteins, and in a vaccine composition, provide a safe and more economic conjugate vaccines.

26 Claims, 7 Drawing Sheets

OTHER PUBLICATIONS

Chu, C. et al., "Further Studies on Immunogenicity of *Haemophilus influenzae* Type b and Pneumococcal Type 6A Polysaccharide–Protein Conjugates," *Infection and Immunity*, 40(1):245–256 (1983).

Schneerson, R., et al., "Serum Antibody Responses of Juvenile and Infant Rhesus Monkeys Injected with *Haemophilus influenzae* Type b and Pneumococcus Type 6A Capsular Polysaccharide–Protein Conjugates," *Infection and Immunity*, 45(3):582–591 (1984).

Geysen, H.M., et al., "The Delineation of Peptides Able to Mimic Assembled Epitopes," *Ciba Foundation Symposium*, 119:130–149 (1986).

Lise, L.D., et al., "Enhanced Epitopic Response to a Synthetic Human Malarial Peptide by Preimmunization with Tetanus Toxioid Carrier," *Infection and Immunity*, 55:2658–2661 (1987).

Milich, D.R., et al., "A Single 10–Residue Pre–S (1) Peptide Can Prime T Cell Help for Antibody Production to Multiple Epitopes Within the Pe–S(1), Pre–S(2), and S Regions of HBsAG," *J. of Immunology*, 138(12):4457–4465 (1987).

Demotz, S., et al., "Delineation of Severasl Dr–Restricted Tetanus Toxin T Cell Epitopes," *J. Of Immunology*, 142(2):394–402 (1989).

Fairweather, N.F., and Lyness, V.A., "The complete Nucleotide Sequence of Tetanus Toxin," *Nucleic Acids Research*, 14(19):7809–7812 (1986).

Francis, M.J., et al., "Non–Responsiveness to a Foot–and–Mouth Disease Virus Peptide Overcome by Addition of Foreign Helper t–Cell Determinants," *Nature*, 300(12):168–170 (1987).

Greenfield, L., et al., "Nucleotide Sequence of the Structural Gene for Diptheria Toxin Carried by Corynebateriophage β," *Proc. Natl. Acad. Sci. USA*, 80:6853–6857 (1983).

Anderson, P., et al., "Immunization of 2–Month–Old Infants with Protein–Coupled Oligosaccharides Derived from the Capsule of *Haemophilus Influenzae* Type b," *J. of Pediatrics*, 107(3):346–351 (1985).

Margalit, H., et al., "Prediction of Immunodominant Helper T Cell Antigenic Sites From the Primary Sequence," *J. Immunology*, 138 (7):2213–2229 (1987).

Bixler, G.S., et al., "T Cell Recognition of Lysozyme: III. Recognition of the 'Surface–Simulation' Synthetic Antigenic Sites," *J. of Immunogenetics*, 11:245–250 (1984).

Jolivet, M.E., et al., "Induction of Biologically Active Antibodies by a Polyvalent Synthetic Vaccine Constructed Without Carrier," *Infection and Immunity*, 55(6):1498–1502 (1987).

Bixler, G.S., et al., "T Cell Recognition of Myoglobin. Localization of the Sites Stimulating T Cell Proliferative Responses by Synthetic Overlapping Peptides Encompassing the Entire Molecule," *J. of Immunogenetics*, 11:339–353 (1984).

Bixler et al, Adv. Exp. Med. Biol., 251, pp.175–80 (1989), Chem. Abs. 113(11), 95766t.

Bigio et al, FEBS Lett., vol. 218(2), pp. 271–6, (1987), Chem. Abs. vol. 107(17), 1495732.

Audibert et al., Proc. Natl. Acad. Sci., vol. 79(16), pp. 5042–6, (1982), Chem. Abs., vol. 97(21), 179864n.

Hu et al, Biochem. Biophys. Acta, vol. 902(1), pp.24–30(1987), Chem. Abs. vol. 107(13), 1107892.

Comanducci et al, Nucleic Acid Res., vol. 15(14), pp. 5897, (1987), Chem. Abs., vol. 107(13), 110183x.

ANALYSIS OF CRM PROTEIN FOR HELICAL AMPHIPATHIC REGIONS

GADDVVDSSKSFVMENFSSYHGTKPGYVDSIQKGIQKPKSGTQGNYDDDWKEFYSTDNKYDAAGYSV
***11111111111110001111000101111111001000000000111010001101001111

DNENPLSGKAGGVVKVTYPGLTKVLALKVDNAETIKKELGLSLTEPLMEQVGTEEFIKRFGDGASRV
0011111000111001001111110000000101111000000011111110111111111111

VLSLPFAEGSSSVEYINNWEQAKALSVELEINFETRGKRGQDAMYEYMAQACAGNRVRRSVGSSLSC
1000000110001011111101100000000000000000111111111111111011111111100100

INLDWDVIRDKTKTKIESLKEHGPIKNKMSESPNKTVSEEKAKQYLEEFHQTALEHPELSELKTVTG
000001111100000000111000000111111111111011101111111111111000000100100

TNPVFAGANYAAWAVNVAQVIDSETADNLEKTTAALSILPGIGSVMGIADGAVHHNTEEIVAQSIAL
11111010111110010111010011111100100001111111111111111111111111110

SSLMVAQAIPLVGELVDIGFAAYNFV(E)SIINLFQVVHNSYNRPAYSPGHKTQPFLHDGYAVSWNTVE
000001111111111000000111111 1 111110111111111111010001111111110111011

DSIIRTGFQGESGHDIKITAENTPLPIAGVLLPTIPGKLDVNKSKTHISVNGRKIRMRCRAIDGVTF
111111000001110000000000000000011101000000000000000000000000000010000

CRPKSPVYVGNGVHANLHVAFHRSSSEKIHSNEISSDSIGVLGYQKTVDHTKVNSKLSLFFEIKS
011000000111000000000111111010000011110111011111110000000000000***

*The analysis was originally marked with a G in the position marked (E); and E in this position does not change the anlysis.

CYCLE 2

CYCLE 5

CYCLE 9

CYCLE 17

CYCLE 22

CYCLE 28

Fig. 6

Antibody Response to RSV F protein.

SYNTHETIC PEPTIDES REPRESENTING A T-CELL EPITOPE AS A CARRIER MOLECULE FOR CONJUGATE VACCINES

RELATED APPLICATIONS

This application is a continuation of application Ser. No. 08/164,989 filed Dec. 9, 1993, abandoned, which is a File Wrapper Continuation of Ser. No. 07/828,711, filed Jan. 31, 1992 (abandoned), which is a Continuation of Ser. No. 07/304,783, filed Jan. 31, 1989 (abandoned), which is a Continuation-in-Part of Ser. No. 07/150,688, filed Feb. 1, 1988 (abandoned).

TABLE OF CONTENTS
1. Field of the Invention 4
2. Background of the Invention 4
   2.1. Vaccines
      2.1.1. Mechanism of B-Cell Activation 6
      2.1.2. B- and T-Cell Cooperation 7
   2.2. Carrier Effect 8
      2.2.1. Carrier Proteins 10
   2.3. T-Cell Determinants 12
3. Summary of the Invention 18
4. Description of the Figures 20
5. Detailed Description of the Invention 21
   5.1. Bacterial T-Cell Epitopes 21
      5.1.1. Techniques for Identification of T-Cell Epitopes 21
      5.1.2. Sources of T-Cell Epitopes 23
      5.1.3. $CRM_{197}$ Epitopes 25
      5.1.4. Preparation of the CRM T-Cell Epitope 27
      5.1.5. Tetanus Toxin Epitopes 28
   5.2. Antigen-T-Cell Epitope Conjugates 28
      5.2.1. Capsular Polymers 30
      5.2.2. Other Antigens 32
      5.2.3. Preparation of Antigen-Epitope Conjugates 32
   5.3. Formulation and Administration of Vaccines 35
6. Examples
   6.1. Procedure for Solid-Phase Peptide Synthesis 37
   6.2. Chemical Characterization of Synthetic Peptides 39
   6.3. T-Cell Activation 41
   6.4. Preparation of HbO-Peptide Conjugates 43
      6.4.1. Polyacrylamide Gel Electrophoresis (PAGE) 44
      6.4.2. Western Blot Analysis 45
      6.4.3. Immunization 46
      6.4.4. Farr Assay 46
      6.4.5. ELISA Assay 47
      6.4.6. Immunoglobulin Class and Subclass Determination 48
   6.5. Generation of Tetanus Toxin Fragments 49
   6.6. Results
      6.6.1. Predicted T-Cell Epitopes of CRM 50
      6.6.2. Analysis of Synthetic Peptides 50
      6.6.3. Western Blot Analysis of PRP-Peptide Conjugates 53
      6.6.4. Immunogenicity Peptide Profile for Murine T-Cell 54
      6.6.5. Peptide Analogue Immunogenicity Profile for Murine T-Cell 57
      6.6.6. Immunogenicity Peptide Profile for Human T-Cell 60
      6.6.7. Anti-Peptide T-Cell Responses 62
      6.6.8. Refinement of T-Cell Boundaries 64
   6.7. Anti-PRP and Anti-CRM Response Elicited by Peptide Conjugates 70
   6.8. Anti-PRP and Anti-CRM Response Elicited by Conjugates Including a Modified Peptide Analogue 75
   6.9. Tetanus Toxin Epitopes 79
7. Antibody Response to Non-Carbohydrate Hapten Antigens 87

1. FIELD OF THE INVENTION

The present invention relates to vaccine compositions comprising an antigen, an antigenic determinant or hapten, conjugated to a carrier molecule. More specifically, the formulations comprise an antigen, antigenic determinant or hapten conjugated to a T-cell epitope of a bacterial product. The present compositions are capable of effectively inducing the production of protective antibodies against the immunogens employed, while at the same time avoiding the use of larger protein carrier molecules.

2. BACKGROUND OF THE INVENTION

The production of a protective immune response against any given infectious agent in vertebrates depends initially on the provision of the appropriate stimulus to the host's immune system. The infectious organism itself typically provides numerous immune-stimulatory compounds, or antigens, by the very nature of its cell membrane compositions, or by the metabolic products it releases in the host's body. These substances, usually larger molecules, such as proteins, lipopolysaccharides or glycoprotein, are recognized by the immune system as foreign, and provoke one or more different types of reaction from the host in an effort to remove or disable the invading organism. The antigen may stimulate sensitized lymphocytes (T-cells) which provide cell mediated immunity. Alternatively, an antigen may also stimulate B-lymphocytes to initiate the synthesis and secretion of free antibody into the blood and other bodily fluids (humoral immunity) and can operate with B-lymphocytes. The development of the body's protective immune response depends upon achieving a threshold level of stimulation of one or both of these systems, i.e., the activation of B-cells with cooperation from activated T-cells (see infra). Temporary immunity against infection can often be provided by giving an individual preformed antibodies from another individual of the same or different species; this is known as passive immunity. An example of such immunity is the protection afforded to a fetus or newborn by placental transfer of maternal antibodies as well as transfer through milk. Another example is the pooled adult gamma globulin that can be used to prevent or modify the effects of exposure to measles, chicken pox, hepatitis, smallpox and tetanus. These acquired antibodies are eventually utilized by interaction with the antigens or catabolized by the body, and thus the protection is eventually lost. A more permanent form of protection is afforded by active immunizations by vaccination, which stimulates the host's own immune system to produce protective antibodies by activation of B- and T-lymphocytes. In brief, vaccination confers an active protective immunity by employing a harmless or non-virulent form of antigen e.g., a killed or genetically altered bacterium, or an isolated polysaccharide or glycoprotein from the cell wall or capsule of the microorganism, as a primary stimulus to the immune system. This provokes a rather slow response in antibody production which peaks and falls off. However, the body has been alerted to the existence of the antigen, and the next time exposure occurs, presumably with the live, virulent organism, a secondary response, with much more rapid and abundant production of antibodies, is observed. This second response will typically be sufficient to prevent the microorganism from establishing itself sufficiently to be able to cause a full-blown infection.

2.1.1. MECHANISM OF B-CELL ACTIVATION

When an antigen enters the body, at least some portion of it may be taken up and digested by phagocytic macrophages; however, other dendritic macrophages (antigen presenting cells or APC's) incorporate the antigen into their surface membrane for the purpose of presentation and activation of lymphocytes. Early in B-cell development, each cell develops a commitment to a particular antigen binding specificity and produces antibody with specificity for the antigen on its cell surface. The first presentation of an antigen to an antigen-specific B-cell results in a slowly rising synthesis of the antibody, usually dominated by IgM. This is the primary response which is the type of response typically stimulated by vaccination; it causes the maturation of the B-lymphocyte into a plasma cell which is highly specialized for antibody production. Upon a second encounter with the same antigen, generally in the form of a challenge by a live microorganism carrying the antigen, the system has already learned to recognize the antigen, and a much more rapid and greater response (secondary response), dominated by IgG, occurs. This "learning" is based in the long-lived memory cells which continue to circulate after the first exposure to antigen; these memory B-cells carry on their surfaces the immunoglobulins which bind strongly with the reinvading antigen, rapidly producing new antibody, and, in the best of circumstances, prevent the infectious agent from causing disease.

2.1.2. B- AND T-CELL COOPERATION

The foregoing discussion presents, in a very general manner, the mechanism for B-cell stimulation and antibody production. In reality, however, the B-cells do not function completely independently in the generation of a protective response. Although T-cells themselves do not secrete antibody, one type of T-cell, helper T-cells, are frequently needed to assist in the stimulation of the B-cell because the interaction of some antigens with surface-bound antibodies alone is frequently insufficient to stimulate B-cell growth and secretion of soluble antibody. The helper T-cells also interact with and recognize antigens on the surface of antigen-presenting macrophages, and develop antigen recognition. The T-cells then recognize antigen on the surface of macrophages and mediate activation and differentiation of resting B-cells. Through the secretion of soluble factors, B-cell growth factors increase the numbers of activated B-cells by interaction with their surface receptors and a maturation factor stops proliferation and stimulates the differentiation to antibody-secreting plasma cells.

Certain specific types of antigens must engage T-cell assistance in eliciting the appropriate response from T-cells. Generally speaking, those antigens in which a determinant appears only once per molecule, such as an asymmetric protein, are highly dependent on T-cell interaction and must rely on its other determinants or T-cell epitopes on the molecule to be recognized by T-cells. The T-cell then presumably sends an accessory signal to the B-cell which helps the antigenic stimulation of the B-cells to be more effective.

2.2. CARRIER EFFECT

Certain types of molecules, such as small peptides or haptens, are inherently poorly immunogenic or weakly immunogenic, failing to produce an antibody response under any circumstances. Other molecules, such as certain bacterial capsular polysaccharides (CP's) may be highly immunogenic in adults, but in the poorly developed infant immune system fail to produce an adequate protective response.

In order to obviate the problems encountered with inducing an immune response with weakly immunogenic molecules, such as small peptides, haptens, CP's and the like, attempts have been made to enhance their immunogenicity by binding them to "carrier" molecules. These carriers are most commonly large immunogenic proteins; the intended effect of these conjugates is to mimic the T-cell cooperative effect that occurs with naturally immunogenic molecules. In other words, the polysaccharide covalently bound to a carrier will elicit T-cell participation in antibody production by the T-cell's response to the presence of the determinants on the carrier. The interaction of the T and B-cells will then proceed in the usual fashion observed, as outlined above with respect to large immunogenic proteins. By engaging the T-cells with carrier determinants, B-cells will begin antibody production not only to the carrier itself, but also to the bound polysaccharide molecule. This approach to increasing immunogenicity of small or poorly immunogenic molecules has been utilized successfully for decades (see, e.g., Goebel, et al., *J. Exp. Med.* 69: 53, 1939), and many vaccine compositions have been described in which purified capsular polymers have been conjugated to carrier proteins to create more effective vaccine compositions by exploiting this "carrier effect".

For example, Schneerson, et al., (*J. Exp. Med.* 152: 361–376, 1980) describe Haemophilus influenzae b polymer protein conjugates which confer immunity to invasive diseases caused by that microorganism. The intent of the conjugation was to overcome the age-related immunological behavior of capsular polymers in infants. The polymers were conjugated to a number of different proteins, including serum albumin, *Limulus polyphemus* hemocyanin, and diphtheria toxin by means of a linking agent such as adipic dihydrazide.

Conjugates of PRP (polyribosyl ribitol phosphate, a capsular polymer of *H. influenzae* b) have been shown to be more effective than vaccines based on the polysaccharide alone (Chu et al., *Infect. Immun.* 40: 245, 1983; Schneerson et al., *Infect. Immun.* 45: 582–591, 1984). The conjugation has also been shown to by-pass the poor antibody response usually observed in infants when immunized with a free polysaccharide (Anderson et al., *J. Pediatr.* 107: 346, 1985; Insel et al., *J. Exp. Med.* 158: 294, 1986).

Geyer et al. (*Med. Microbiol. Immunol.* 165: 171–288, 1979) prepared conjugates of certain *Klebsiella pneumoniae* capsular polysaccharide fragments coupled to a nitro phenyl ethylamine linker by reductive amination, and the derivatized sugar was then attached to proteins using azo coupling.

2.2.1. CARRIER PROTEINS

That the use of the carrier principle constitutes an effective method of improving vaccines containing capsular polymers is widely accepted. However, these polymer protein conjugates are not without their disadvantages, particularly for human use. For example, the number of proteins which are ethically accepted for use as potential carrier proteins for human administration is relatively limited. The two primary proteins currently available for human use are tetanus toxoid and diphtheria toxoid. Another valuable carrier protein is $CRM_{197}$, a protein having a single amino acid change from native diphtheria toxin, but which is inherently non-toxic and retains immunogenicity substantially identical to the native protein. Numerous considerations also affect the routine use of these known carrier proteins. For example, the limited number of available proteins means that a large number of vaccine products will be based on one of these proteins; multiple vaccinations with materials conjugated with this limited number of carriers increases the probability that undesirable reactions to these proteins may occur following repeated immunization. The presence of pre-existing antibodies may also induce adverse local or systemic immunologic sensitivity reactions. Further, the possibility also exists that a protein contained in the conjugate may cross-react with normal host tissue thereby raising the possibility of auto-immune type phenomena. It is also possible that the phenomenon of epitopic suppression may occur with the use of conjugate vaccine. Briefly, this phenomenon, first described for keyhole limpet hemocyanin conjugates by Herzenberg et al. (*J. Exp. Med.* 155: 1741, 1982), and data reported for tetanus toxoid conjugates by Joliet et al. (*Biochem. Biophys. Res. Comm.*, 117: 359, 1983) and Schulte et al. (*J. Immunol.* 135: 2319, 1985), is observed when immunity to a protein contained in the conjugate already exists in the vaccinee, and interferes with the generation of a response to the covalently coupled polysaccharide. Although not yet documented in humans, this suppression (if it occurs) may potentially have serious implications in the development of conjugate vaccines.

Finally, since the proteins are the products of a biological process, there are several inherent difficulties. First, as a product of a biological system, there will be an unavoidable lot-to-lot variation; this variation may potentially alter the T-cell-dependent characteristics of the protein or its overall antigenicity. Thus, more stringent monitoring of the production is required with an associated increase in cost. Second, there are the obvious increased costs involved in the preparation and purification of a biological product.

Clearly there is a necessity for an alternative to the currently available conjugate vaccines which will obviate the immunological difficulties attendant upon the use of these vaccines and yet retain substantially the same immunogenicity as the known effective vaccines. We have now shown that it is possible to obtain such a vaccine by the conjugation of an antigen, antigenic determinant or hapten with a T-cell epitope of a bacterial product.

2.3. T-CELL DETERMINANTS

At the present time, it is not yet clear how T-cells recognize proteins, or what the T-cell recognizes as an immunogenic determinant.

For several years it has been generally agreed that antigenic antibody-binding determinants of proteins exhibit two distinct architectures. Determinants of a protein may exist as short segments of the primary sequence containing amino acids directly linked by peptide bonds. Such determinants have been termed "sequential" or "continuous" determinants. Alternatively, a determinant may be composed of amino acids which are distant in primary sequence but which are spatially in close proximity because of secondary folding. Determinants exhibiting this architecture have been termed "topographic" or, less ambiguously, "discontinuous" determinants. In addition, there is general agreement that antibodies recognize accessible surface regions of a protein which are conformationally dependent and have a minimum length of 5–7 amino acid residues.

T-cell recognition of proteins is a more complex process than antibody binding and consequently is less clearly understood. T-cells have generally been regarded as recognizing continuous determinants. Many years ago it was demonstrated that T-cells could recognize both the native and denatured form of a protein whereas antibody could not (Maizels et al., *Eur. J. Immunol.* 10: 509, 1980). This finding was interpreted as showing exclusive recognition of sequential determinants by T-cells and demonstrating a dichotomy between T and B-cell recognition of proteins (Maizels et al., supra). Although not settled, however, the notion that T and B-cells recognize fundamentally different structures still persists (Benjamin et al., *Ann. Rev. Immunol.* 2: 67, 1984).

The controversy over what is recognized as a determinant by a T-cell also extends to how a T-cell perceives a protein. It is very well established that the immune system recognizes a protein in a genetically restricted manner and that T-cells perceive proteins in the context of an Ia molecule on the surface of an antigen presenting cell. It has been suggested that the APC encounters the protein first, internalizes it and digests the protein into smaller fragments. The small fragments of the original protein are then expressed in the context of Ia on the surface of an APC where it can be recognized by T-cells. The T-cell would, therefore, only see a "processed" peptide fragment.

Although it is still not clear what a T-cell perceives, there is agreement among several groups using a variety of models that a region of 7–17 amino acid residues is required for recognition. As early as 1972, it was demonstrated that a 7 residue poly-L-lysine polymer induces delayed type hypersensitivity in guinea pigs (Schlossman, *Transplant. Rev.* 10: 97, 1972). More recent studies with a variety of natural proteins including fibrinopeptide, influenza hemagglutinin, cytochrome, lysozyme, ovalbumin and myoglobin, have indicated a minimal peptide size for T-cell stimulation of 7–17 amino acid residues. Using T-cell clones of known specificity, a size of 10–14 residues was found to be required for a T-cell response (Atassi, et al., *Biochem. J.* 246: 307–312, 1987). The larger peptide size required for T-cell recognition, in comparison to the 5–7 residues required for antibody binding, may reflect the additional residues required for the expression of the determinant in context of an Ia molecule.

Indeed, the interaction of Ia and synthetic peptides has been demonstrated in several models. A region involved in Ia binding, an agretope, was postulated (Katz, et al., *J. Mol. Cell Immunol.* 1: 3, 1983). Subsequently, planar membranes with Ia incorporated have been used to present synthetic peptides to T-cells (Watts et al., *PNAS* 81: 7564, 1984). More recent studies, have shown the direct binding of synthetic peptides to Ia molecules (Babbett et al., *Nature* 317: 359, 1985; Buss *PNAS* 83: 3968, 1986) which were presented in a genetically restricted manner depending on the origin of the Ia molecules (Groillet et al., *Science* 235: 865, 1987). Largely because of these studies, it has been postulated that a T-cell epitope would consist of a hydrophilic region which can interact with T-cell receptors and a hydrophobic agretope that binds to Ia molecules. In addition, it is assumed that these fragments representing continuous determinants would be generated by proteolytic processing of the original protein.

In attempting to predict the locations of antibody binding or T-cell determinants, several different approaches have been employed. Several years ago, Hopp and Woods (*PNAS* 78: 3824; 1981; European Appln. No. 0056249; South African Patent No. 823952) assigned a numeric hydrophobic/hydrophilic index to each of the amino acids and examined the primary sequence of several proteins in the context of this index. According to their analysis, the known antibody binding sites of the proteins examined correlated with hydrophilic regions. A similar approach was adopted by Kyte and Doolittle (*J. Mol. Biol.* 157: 105–132, 1982) using a numeric index of slightly different derivation.

More recently, attempts have been made to correlate regions of a protein having high flexibility or segmental mobility with regions of antibody binding (Tainer et al., *Nature* 315: 327, 1985; *Ann. Rev. Immunol.* 3: 501, 1985, Westhoff et al., *Nature* 311: 123, 1984). In this approach, data derived from X-ray or neutron diffraction patterns provides an estimate of the relative conformational variability of a residue which is expressed as an atomic temperature factor. A graph of the atomic temperature factor versus the residue number indicates the relative degree of mobility along the polypeptide chain for a given protein. Regions of high mobility were thought to correlate with known antibody binding sites (Tainer et al., supra.).

T-cell determinants have been viewed by some groups as exhibiting amphipathic structure, that is, a determinant is thought to be composed of a hydrophilic region which binds to the T-cell receptor and also a hydrophobic region to bind to Ia molecules. A 16 residue T-cell determinant of lysozyme was found to be composed of a short, consecutive series of hydrophilic residues (Allen et al., *PNAS* 81: 2489, 1984). Others, however, have suggested that T-cell determinants have a tendency to form stable helical structures in which the hydrophilic residues align on one surface of the helix while hydrophobic residues align on the opposing surface (DeLisi and Berzofsky, *PNAS* 82: 2489, 1985; Watts et al., *PNAS* 82: 7048, 1985). An algorithm to search a given protein sequence for regions with a tendency to form helical amphipathic structures has been developed (DeLisi and Berzofsky, supra.) and applied to several protein models. In contrast, some investigators maintain that T-cell determinants are associated with beta turns within the protein (Katz, et al., *J. Immunol.* 135: 1386, 1985). A clear picture of what factors are important to the prediction of a T-cell determinant is yet to emerge.

Several groups have recognized the importance of including a T-cell determinant as part of a synthetic vaccine. Milch et al. (U.S. Pat. Nos. 4,599,230 and 4,599,231) have synthesized a peptide vaccine composed of T-cell and B-cell determinants of the hepatitis B virus surface antigen. Similarly, a malaria vaccine constructed of a T-helper epitope of the circumsporozoite protein was covalently linked to the major B-cell determinant of this protein (Good et al., *Science* 235: 1059, 1987). Interestingly, the T helper determinant was predicted by the algorithm of DeLisi and Berzofsky, supra. Both of these reports, employed T-cell and B-cell determinants from within the same protein to construct the vaccine. In contrast, Leclerc et al., (*Eur. J. Immunol.* 17: 269, 1987) constructed a vaccine by copolymerization of a streptococcal peptide, S-34, containing within its sequence both T- and B-cell determinants with a viral peptide representing a B-cell determinant from hepatitis B virus. The T-cell determinant, which in this case corresponded substantially to a native peptide, conferred immunogenicity to the viral peptide thereby functioning as a carrier molecule.

3. SUMMARY OF THE INVENTION

The present invention provides novel isolated or synthetic T-cell epitopes of bacterial products; such epitopes are useful in the preparation of vaccine compositions analogous in their utility to previously known vaccines which utilized carrier proteins to enhance antibody production. Among these epitopes are those isolated from bacterial toxins, specifically diphtheria toxin or crossreactive material (CRM), and tetanus toxin. As used herein, and in the claims, the T-cell epitopes of the invention shall refer to T-cell epitopes per se.

The T-cell epitopes can be used in combination with an unrelated B-cell determinant to obtain significant quantities of antibody production against the B-cell determinant without the production of antibodies to the T-cell epitope. It has now been surprisingly discovered that such a combination can provide substantially as effective a level of antibody production as does the B-cell determinant-carrier protein combination now commonly used. The availability and demonstrated utility of such a combination now makes it possible to avoid the potentially undesirable immunological consequences which may be associated with the use of carrier-protein based vaccines. Further, the use of the T-cell epitope per se, as opposed to a larger peptide containing the epitope, provides an economic advantage in that it may be readily synthesized as well as a safety advantage in avoidance of use of the whole protein.

The invention also provides new conjugates comprising an isolated or synthetic T-cell epitope conjugated to an antigen, an antigenic determinant, or hapten. The conjugation of the two elements in a vaccine composition enables a more efficient level of antibody response to the antigen. These vaccines are useful in the production of antibodies to any type of antigen, including not only antigens related to pathogenic organisms (bacteria, viruses, parasites), but also to allergens, and cancer-related antigens, and the like. However, the conjugates are particularly useful in the formulation of vaccine compositions utilizing antigens which are only weakly immunogenic, i.e., those antigens which have traditionally had to be conjugated to carrier proteins in order to achieve a satisfactory level of antibody production.

The availability of these conjugates also provides a method for stimulating an immune response in warm-blooded animals which comprises administering to the animal an immunogenically effective amount of an antigen of interest conjugated to a T-cell epitope of a bacterial product. The method encompasses protective immunization in the traditional sense, i.e., inoculation against a particular microbial pathogen; but it also is intended to encompass any other type of treatment in which increase in antibody production would be desired, e.g. the present method may be used in stimulation of antibodies against tumor-specific or tumor associated antigens, or in the production of antibodies against common allergen. The method is also particularly useful in the immunization of infant humans whose immune system is not fully developed. The present method may be used in both a therapeutic and prophylactic context.

4. BRIEF DESCRIPTION OF THE DRAWINGS

FIG. 1 shows the primary sequence of CRM in standard single letter code. Those regions having a tendency to form amphipathic helical structures are denoted by the number 1, and those sequences having potential T-cell epitope activity are underlined.

FIGS. 2A and 2B show HPLC analysis of peptide 6. A. Chromatogram of crude peptide 6. The bar indicates pooled regions. B. Rechromatography of peptide 6 (pooled fractions obtained from above). The synthetic peptide was eluted as described in the text.

FIGS. 3A–3B show selected chromatograms of PTH-derivatives of synthetic peptide 6. The peptide was sequenced as described in the text. The numbers indicate the Edman cycles. Peaks a and b, which serve as internal markers, represent N'N-dimethyl-N'-phenylthiourea and N'N-diphenylthiourea, respectively. Cycle 2 indicates the presence of tyrosine; cycle 5, valine; cycle 9, isoleucine; cycle 17, asparagine; cycle 22, proline and cycle 28, glycine.

FIG. 4 shows Western blot analysis of selected peptide conjugates which were detected with monoclonal antibody to PRP. From left to right, the lanes contain the molecular weight standard (LMW), PRP (peptide 357-380), PRP (peptide 306-334), PRP-CRM, PRP and PRP short (peptide 366-383).

FIG. 6 shows a diagrammatic representation of the antibody response to Respiratory Syncytial Virus (RSV) F protein conjugates.

5. DETAILED DESCRIPTION OF THE INVENTION

5.1. BACTERIAL T-CELL EPITOPES

Figure 2A:
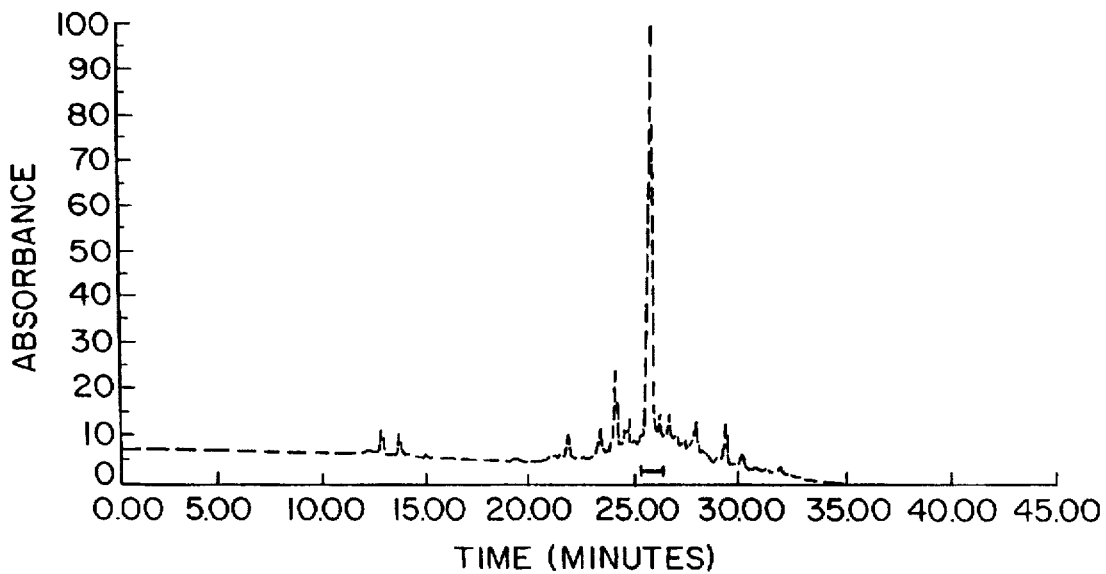

The various embodiments of the present invention revolve around the discovery that isolated or synthetic T-cell epitopes of bacterial products can serve as effectively as carrier proteins for antigens for immunization purposes. It has not previously been demonstrated that the T-cell determinant of a bacterial product, when bound to an antigen, can function in the same manner as the whole native protein conjugated to the same antigen. The knowledge that a T-cell epitope of a bacterial product can function as effectively as a carrier protein in promoting an antibody response has opened the door to an entirely new class of vaccines based on the use of the isolated T-cell epitopes in combination with a B-cell determinant or whole antigen. The following discussion provides a detailed description of means of identification and isolation of appropriate T-cell epitopes for use in the present invention. In addition to having similar immunogenic properties, the use of the epitopes (as opposed to the use of an intact native protein) may obviate the potential problems of hypersensitivity, auto-immunity, and extensive purification, without sacrificing effectiveness.

5.1.1. TECHNIQUES FOR IDENTIFICATION OF T-CELL EPITOPES

Although T-cell epitopes of bacterial products have not been previously identified, there are multiple methods described in the literature which may be applied to the identification of a T-cell epitope or epitopes within a bacterial product of interest. For example, DeLisi et al. (PNAS 82: 7048, 1985; see also Margalite et al., J. Immunol. 138: 2213, 1987) have suggested that potentially epitopic regions may be located by identification of potential amphipathic alpha helical regions in the molecule. Rothbard et al. (Modern Trends in Human Leukemia VII, 1986) also describe an empirical approach to identification of T-cell epitopes by examining the proteins primary sequence with regard to hydrophobicity, charge, polarity and the presence of glycine or proline residues. A sequence in which a charged or glycine residue was followed by two hydrophobic residues was suggestive of a potential T-cell epitope. Bixler et al. (Immunol. Comm. 12: 593, 1983); J. Immunogenet. 11: 245, 1984; J. Immunogenet. 11: 339, 1984) describe a strategy of synthesizing overlapping synthetic peptides encompassing an entire protein molecule for delineation of T-cell epitopes. A new synthetic method described by Gysen (Ciba Foundation Symposium 119: 130, 1986) enables synthesis of a large variety of peptides of small quantities which permit the mimicking of a variety of potential binding sites, in turn allowing rapid scanning of a molecule. More traditional methods, such as enzymatic or chemical digestion of proteins provide peptide fragments which may be readily tested for T-cell activity. For example, enzymes such as chymotrypsin, elastase, ficin, papain, pepsin, or trypsin provide limited and predictable fragments by cleavage of specified amino acid linkages. Similarly, chemical compounds such as N-chlorosuccinimide BPNS-skatole, cyanogen bromide, formic acid, or hydroxylamine, also produce definable fragments by their action on proteins. The presence of the desired T-cell stimulating activity in any given fragment can be readily determined by subjecting purified fragments to a standard T-cell proliferation assay or by analyzing unpurified fragments with a T-cell Western assay (Young et al., Immunol. 59: 167, 1986).

5.1.2. SOURCES OF T-CELL EPITOPES

There are a number of bacterial products which provide convenient sources of potentially useful T-cell epitopes by virtue of the utility of the native parent molecule as a carrier protein. For example, outer membrane proteins from various gram-negative bacteria may be employed, such as OMP from Haemophilus influenzae. The pili (fimbriae), the filamentous, non-flagellar appendages found on many gram-negative bacteria, as well as flagellin, the protein component of bacterial flagella, represent a potential source of T-cell determinants. Filamentous hemagglutinins (FHA) of certain bacteria, e.g., pertussis, are also contemplated as T-cell determinant sources.

Among the most valuable bacterial proteins for the present purposes are the well-known bacterial toxins which have been successfully used as carrier proteins in traditional vaccine compositions. Although the bacterial toxins and toxoids noted above have been used for years to immunize humans, very little is known about their recognition by the immune system. What little has been described in the literature has been inconclusive. Triebel et al. (Eur. J. Immunol. 16: 47, 1986) examined human peripheral leukocytes for T-cell reactivity to fragments of diphtheria toxin generated by cyanogen bromide cleavage. Only a limited set of large fragments was considered, however, and precise delineation of T-cell determinants was not possible. Therefore, a precise T-cell determinant of a bacterial toxin has not yet been identified.

The present preparation of bacterial toxin T-cell determinant conjugates may be based on any of the known toxins which are generally useful in their native form as carriers for antigenic compounds which are only weakly immunogenic. Among the known bacterial toxins, CRMs or toxoids are those of Pseudomonas, Staphylococcus, Streptococcus, Pertussis, and enterotoxigenic bacteria, including *E. coli*. The most widely accepted carrier proteins, however, are tetanus and diphtheria toxoid, which have an established history of safety. A particularly preferred T-cell epitope is isolated from $CRM_{197}$, a non-toxic mutant of diphtheria toxin.

5.1.3. $CRM_{197}$ EPITOPES

"Cross-Reacting materials" or CRMS are genetically altered proteins which are antigenically similar to the native protein toxin and yet are non-toxic. The CRM of diphtheria toxin has already proven to be effective in enhancing the antibody response to bacterial capsular polymers (Anderson et al., *J. Pediatr.* 107: 346, 1985). The cross reacting material known as $CRM_{197}$ is noteworthy as it has a single amino acid change and is immunologically indistinguishable from the native diphtheria toxin. A culture of *Corynebacterium diphtheriae* strain C7 (β 197), which produces $CRM_{197}$ protein, has been deposited with the American Type Culture Collection, Rockville, Md. and has been assigned Accession Number ATCC 53281.

In order to localize potential T-cell determinants within CRM, attention was focused on helical amphipathic regions of the protein according to the theory of DeLisi and Berzofsky (*PNAS* 82: 2489, 1985). The location of discrete regions of potential amphipathic structure were determined by algorithm on a personal computer and validated by comparison of the results obtained for the analysis of sperm whale myoglobin as described in DeLisi & Berzofsky, supra. The program was then applied to the known sequence of $CRM_{197}$ (Collier, *Bacteriol. Rev.* 39: 54, 1975; Drazin et al., *J. Biol. Chem.* 254: 5832, 1979). Six regions of CRM were selected for detailed study. These regions were synthesized by standard step-wise solid phase Merrifield synthesis.

Once a given region of CRM was verified experimentally as containing a T-cell determinant or a portion thereof, the precise boundaries of the determinant could be mapped. This was accomplished by using several different sets of synthetic peptides which systematically dissect the region of interest. In the first set of peptides, the N-terminal of the peptide was varied by successive additions of 3–5 natural sequence residues at a time while maintaining a fixed C-terminal. This enables a crude approximation of the N-terminal boundary. To further refine the location of the boundary, a second series of peptides which dissected this region were synthesized by single step additions of the natural sequence residue to the N-terminal. In the third set of peptides, the C-terminal residues were successively deleted in 1–3 residue steps while maintaining a fixed N-terminal boundary. Since this results in progressively shorter peptides which could adversely affect their recognition, it was necessary to compensate for the decreasing size by addition to the N-terminal of additional residues unrelated to the natural sequence of the protein. With both the N- and C-terminals of the determinant mapped, a peptide corresponding to the delineated region was synthesized and verified as a T-cell determinant.

Of the regions delineated in FIG. 1 as possible T-cell epitopes, the peptide in region 357-383, showed a substantial response in stimulating diphtheria (DT)primed lymph node cells. Further studies localized the epitope to 369-383 of $CRM_{197}$. The sequence represents a T-cell epitope of $CRM_{197}$ and diphtheria toxin. The peptide, when covalently coupled to the capsular polymer PRP, has been shown to be effective in eliciting the desired antibody response to PRP in vivo, and also does not induce antibodies which crossreact with the entire CRM or DT toxin. Thus, this peptide has the characteristics desirable in a bacterial toxin conjugate. Another T cell epitope has been localized to 306-334 of CRM.

5.1.4. PREPARATION OF THE CRM T-CELL EPITOPE

As will be noted by reference to the Examples, infra, a number of variations on the length of the peptide can be made without affecting the activity of the T-cell response, and it is contemplated that the present invention encompasses any of the fragments of the peptide which retain stimulatory activity, but which do not cause the adverse immunological reactions which may be induced by the native proteins. It is also contemplated that the present invention encompasses variations in the active peptide in which amino acid substitutions are made in the primary sequence, without affecting the activity of the peptide. Such substitutions are well known to the skilled artisan. For example, substitutions may be made on the basis of similarity in polarity, charge, solubility, hydrophobicity, hydrophilicity and/or the amphipathic nature of the residues involved. Negatively charged amino acids include aspartic acid and glutamic acid; positively charged amino acids include lysine and arginine; amino acids with uncharged polar head groups or non-polar head groups having similar hydrophilicity values include the following: leucine, isoleucine, glutamine, serine, threonine, phenylalanine, tyrosine.

The method of preparation may be selected from any of those known in the art for peptide synthesis. Among the more commonly used techniques are coupling via the solid phase Merrifield synthesis (*J. Am. Chem. Soc.* 96: 2986–2983, 1964) in which a protected amino acid is bound to a resin particle. Amino acids having functional groups, e.g. tyrosine, are generally protected with an easily removed blocking group. Each of these techniques is equally suitable for the present purpose.

5.1.5. TETANUS TOXIN EPITOPES

In addition to the identification of $CRM_{197}$ T-cell epitopes, the tetanus toxin molecule was also examined for the presence of T-cell epitopes. In order to localize such epitopes, the tetanus toxin molecule was cleaved into sizable fragments using a variety of proteases. Fragments generated in this manner were initially tested for their ability to stimulate murine T-cell proliferation. A set of overlapping peptides encompassing the active fragments were synthesized and tested for T-cell activity. Preferred epitopes are the peptides 961-980 and 1021-1040 of tetanus toxin.

5.2. ANTIGEN-T-CELL EPITOPE CONJUGATES

The T-cell epitopes of the present invention can be valuably combined with virtually any antigen, antigenic determinant, or hapten of medical or veterinary interest, for which an increase in immunogenicity would be desirable. For example, these antigens may be associated with infectious agents of bacterial, viral, parasitic, or fungal origin; examples include pneumococcal polysaccharides, gonococcal outer membrane proteins, adhesion proteins of *Mycoplasma pneumoniae*, or surface saccharides associates with lipopolysaccharide of gram negative bacteria. Additional antigens of this type will be readily recognized by the skilled artisan.

Another group of antigenic materials which can be employed as the B-cell portion of the immunogenic conjugates are any of the known allergens. Examples of the types of allergens which would prove useful in the present invention are B-cell determinants of ragweed (Atassi et al., *FEBS Letters* 188: 96, 1985), rye grass (Standring et al., *Int. Arch. Allergy Appl. Immunol.* 83: 96, 1987); mite proteins Der pI and Der f (Chapman et al., *J. Immunol.* 139: 1479, 1987); carbohydrate epitope of honey bee venom phospholysate $A_2$ (Weber et al., *Allergy* 42: 464, 1987); penicilloyl determinants (Ahlstedt et al., *Int. Arch. Allergy App. Immunol.* 61: 91, 1980); carbohydrate epitopes of sea squirts (Oka et al., *J. Allergy Clin. Immunol.* 80: 57, 1987); and Ascaris antigens (Darden et al., *Immunol. Comm.* 7: 393, 1978).

Also included within the scope of the present invention are tumor-associated antigens. Among the better-characterized antigens are carcinoembryonic antigen (Kuroki et al., *Cancer Res.* 46: 300, 1986; Laferti & Krantz, *Mol. Immunol.* 20: 421, 1983), adenocarcinoma-associated antigen DU-DAN-2 (Lan et al., *Cancer Res.* 45: 305, 1985), and gastrointestinal/pancreatic associated antigen (Magnani, et al., *Cancer Res.* 43: 5489, 1983).

Also of potential interest are various antigens associated with autoimmune diseases, such as rheumatoid arthritis and lupus erythematoses.

It is to be understood from the above discussion, that the use of the term antigen is meant to imply either the whole antigen or one of its determinants, and is also meant to encompass hapten molecules which could benefit by an increase in the immune response which occurs with conjugation to a bacterial T-cell epitope. The foregoing list of antigens is for exemplary purposes only, and additional useful antigens will be readily recognized by one skilled in the art.

5.2.1. CAPSULAR POLYMERS

As has been previously noted, bacterial capsular polymers are among the groups of antigens which have potential to be effectively employed in a vaccine but which are only weakly immunogenic in young humans. As used in this application, the term "capsular polymers" refers to sugar-containing polymers, such as polymers of sugars, sugar acids, amino sugars, polyhydric alcohols and sugar phosphates, and does not refer to amino acid-containing polymers. These "capsular polymers" are frequently referred to in the medical literature as "capsular polysaccharides" though they may contain linkages other than glycosidic linkages and constituents other than sugars such as those listed above.

The capsular polymers (CP) can be derived from many different types of bacteria. These types include *Haemophilus influenzae*, Streptococcus species including *pneumoniae* (particularly serotypes 1, 4, 5, 6A, 6B, 9V, 14, 18C, 19F, and 23F) *pyogenes* and *aglactiae*, *Neisseria meningitidis*, *Klebsiella pneumoniae*, *Pseudomonas aeruginosa* and *Staphylococcus aureus*.

The CP of different bacteria vary widely in immunogenicity in the first year of human life. Some are moderately active, such as *Streptococcus pneumoniae* serotype 3 and *Neisseria meningitidis* serogroup A. The susceptibility to systemic infection by encapsulated bacteria is greater in the first year of life. The immunogenic response to many bacterial capsular polymers in children is age dependent, i.e., immunocompetence to CP increases to adult levels by about six years of age.

Among the inactive CPs are those of *Haemophilus influenzae* type b, *Streptococcus pneumoniae* serotypes 6 and 12, and *Neisseria meningitidis* serogroup C. Examples of CPs which stimulate an intermediate response in infants are *Streptococcus pneumoniae* serotypes 19 and 51. There are also polysaccharides found in organisms, such as *Neisseria meningitidis* serogroup B, which are not immunogenic in any age group.

Non-bacterial polymers can be derived from yeast and fungi, for example, *Crytococcus neoformans*, or saccharide units found uniquely on cancer cells or those found associated with allergens.

5.2.2. OTHER ANTIGENS

Other antigens useful in the preparation of an immunogenic construct include antigens selected from the group consisting of microbial antigens, viral antigens, tumor antigens, allergens, and auto-immunity related antigens.

Examples of microbial antigens include the outer membrane proteins (e.g., from *Haemophilus influenzae* or *Branhamella catarrhalis*) and surface proteins (e.g., the M protein from *Streptococcus pyogenes*). Examples of viral proteins include the F and G proteins of Respiratory Syncytial Virus (RSV).

5.2.3. PREPARATION OF ANTIGEN-EPITOPE CONJUGATES

The antigen-epitope conjugates of the present invention may be prepared by any of the biologically acceptable methods known in the art for coupling of antigens to carriers. In order to ensure the most efficient exploitation of the present conjugates, the method of coupling is most preferably covalent coupling. Many such methods are currently available for coupling of poly- and oligo-saccharides, proteins, and peptides to peptide carriers. Most methods create either amine or amide bonds, or in some cases thio-esters.

Coupling chemistries can be altered, to some extent, through the synthesis of modified analogues of a T-cell epitope. Such modifications can include, for example, the addition of lysine or cysteine to the N-terminal of the peptide with or without a spacer element. The capacity of such analogues to stimulate T-cells has been compared with that of the non-modified peptide.

(a) Polysaccharides or Oligosaccharides to Peptides

One useful method for saccharide coupling is reductive amination. Poly and oligosaccharides have free reducing end groups which can be reductively aminated to the nitrogen of the N-terminal amino acid or ε-amino groups of lysine of the peptide. The bond formed is a secondary amine. Alternatively the poly or oligosaccharide can be oxidized, for example, by periodate ion to give internal and/or terminal aldehyde functions. The aldehyde groups also can be reductively aminated to the N-terminal amino acid or to the ε-amino groups of lysine in the peptides.

Short bifunctional spacer groups having an amino group at one end and an active group such as amino, masked aldehyde, carboxylic acid or active ester or thio group at the other end can be reductively aminated to the saccharide and then coupled to the peptide through the other end group of the spacer, α-amino caproic acid 4-aminobutyl dimethylacetal are examples of such a spacer group.

Reaction of terminal reducing sugars with O-phenylenediamine and nitrophenylhydrazines gives substituted 1-phenylflavazoles. Coupling of the functionalized saccharides to peptides is through the conversion of the nitro group to a diazo function.

Activation of saccharide hydroxyl groups is an alternate method. Hydroxyl groups of saccharides can be activated by the use of either cyanogen halide (normally cyanogen bromide) or carbonyl diimidazole to give a derivatized hydroxyl that can couple to the N-terminal amino or ε-amino groups of the peptide. The bond formed is either an isourea or carbamate.

As an additional method, saccharides having carboxylic acid functional groups, such as uronic acid groups or aldonic acid functions can be coupled to N-terminal amino and ε-amino groups of lysine of peptides by activation of the carboxyl groups by the formation of active esters using carbodiimides or isobutylchlorocarbonates. The resulting bond is an amide linkage.

Also, polysaccharides or oligosaccharides having free amino groups can be coupled to peptides either through the carboxyl terminal or N-terminal amino acid. Coupling to the carboxyl terminal end or to amino acids such as glutamic acid is by activation of the carboxyl acid function with carbodiimides as described above. Coupling to the N-terminal nitrogen or lysines is accomplished by using a bifunctional spacer group such as disuccinimidyl substrate that reacts at each end with amino functions.

(b) Proteins or Peptides to Peptides

Carboxylic acid functions can be activated by carbodiimides or chlorocarbonates to give active esters that can be reacted with amino groups on the peptide. The resulting bond formed is an amide.

The more general method of coupling proteins or peptides to peptides is by the use of bifunctional crosslinking reagents. These are small spacer molecules having active groups at each end. The spacer molecules can have identical or different active groups at each end. The most common active functionalities, coupling group and bonds formed are:

1. Aldehyde - amino - secondary amine
2. Maleimido - sulfhydryl - thio ether
3. Succinimido - amino - amide
4. Imidate esters - amino - amide
5. Phenyl azides - amino - phenyl amine
6. Acyl halide - sulfhydryl - thio ether
7. Pyridyldisulfides - sulfhydryl - disulfide
8. Isothiocyanate - amino - isothiourea.

5.3. FORMULATION AND ADMINISTRATION OF VACCINES

The present conjugates are useful in the preparation of vaccine compositions for treatment of any type of microbial infection. The conjugates may be combined with any of the commonly used pharmaceutically acceptable carriers, such as water, physiological saline, ethanol polyols (such as glycerol or propylene glycol), or vegetable oils, as well as any of the vaccine adjuvants known in the art. They may also be incorporated into liposomes. As used herein, "pharmaceutically acceptable carriers" include any and all solvents, dispersion media, antibacterial and antifungal agents, isotonic and absorption-delaying agents and the like. Supplementary active ingredients may also be employed.

The mode of administration is typically parenteral, i.e., intravenous, intramuscular, intraperitoneal or subcutaneous. Oral administration is also possible. The amount of conjugate employed in such vaccine will vary depending upon the identity of the antigen employed. Adjustment and manipulation of established dosage ranges used with traditional carrier conjugates for adaptation to the present conjugate vaccines is well within the ability of the skilled artisan. For example, the typical dosage of the known carrier conjugates comprising PRP and CRM is approximately 1–25 µg of peptide. The present vaccines and methods are also particularly useful because most infants have already been "primed" by administration of diphtheria and tetanus vaccines shortly after birth. The conjugates of the present invention are intended for use in the treatment of both immature and adult warm-blooded animals, and in particular humans. Those diseases for which effective prevention may be achieved with the present method will be obvious to the skilled artisan upon reading the present disclosure. Also, the use of the present methods and conjugates is not limited to prophylactic application; therapeutic application is also contemplated.

In a preferred embodiment, the conjugate comprises a bacterial capsular antigen, or an antigenic fragment thereof, conjugated to the T-cell epitope of a diphtheria toxin. This combination is useful in the treatment of meningitis. This condition, most commonly caused by $H.$ $influenzae$ b, occurs in children less than 6 years of age, with about 60% of cases occurring in children under 2 years of age. Protection against this disease has been difficult to achieve in infants under 18 months with traditional vaccine compositions. The present compositions, however, produce a substantial level of antibody production due to T-cell recruitment.

The following non-limiting examples provide a demonstration of the preparation and effectiveness of the present T-cell epitope conjugates.

6. EXAMPLES

6.1. PROCEDURE FOR SOLID-PHASE PEPTIDE SYNTHESIS

Synthetic peptides were constructed using the stepwise solid-phase approach of Merrifield (1963) on an Applied Biosystems Model 430A Peptide Synthesizer. All synthetic peptides were assembled on an insoluble co-polymer resin consisting of styrene and divinylbenzene. All amino acids used in the assembly of these peptides were supplied with the α-amino group protected by a t-BOC(t-butyloxycarbonyl) moiety. The peptide chains are attached to the resin through a "PAM" (phenylacetamido) linker.

The principle of solid phase synthesis is briefly described as follows. One equivalent of the t-BOC protected amino acid stored as a dry powder in an individual vial, is dissolved with dichloromethane (DCM), and transferred to the Activator vessel where it is activated with half equivalent of dicyclohexyl carbodiimide (DCC) to give the (α-amino protected, t-BOC) amino acid symmetric anhydride which is utilized as the acylating species. The symmetric anhydride derivative is transferred into the concentrator vessel while the insoluble byproduct, dicyclohexylurea, is dissolved with methanol-DCM and flushed away from the activator vessel. In the concentrator vessel, DCM is removed and replaced with N,N dimethylformamide (DMF), which is the solvent used to increase the efficiency of the coupling reaction between the symmetric anhydride and the peptides assembled on loaded PAM-resins. After the solvent exchange, the symmetric anhydride is then added to the reaction vessel. Prior to the delivery of the symmetric anhydride in DMF, the peptide-resin in the reaction vessel has been N-(alpha)-deprotected with TFA/DM C mixture, washed with DCM, and neutralized with N,N-diisopropylethylamine/DMF solution. After the addition of symmetric anhydride to the reaction vessel, the coupling reaction is carried out, resulting in the covalent attachment of the activated carboxyl of the t-BOC amino acid to the deprotected α-amino group of the resin-bound peptide. When synthesis is completed, the reaction vessel is drained followed by washing with DM C, thus preparing the peptide-resin for another cycle of synthesis.

The symmetric anhydride derivatives were used as the acylating species for most amino acids except for asparagine, glutamine, and arginine. These three amino acids were coupled as 1-hydroxybenzotriazole esters. The reactive side chains of amino acids were protected during the synthesis of the peptide chains. The protecting groups used were O-benzyl for Asp, Glu; benzyl for Ser, Thr; 4-methyl-benzyl for Cys; tosyl for Arg, His; 2-Cl-carbobenzoylcarbonyl for Lys; O-(p- bromobenzyoxycarbonyl) for Tyr; formyl for Trp. The completeness of coupling at each step was monitored by a quantitative ninhydrin assay (V. K. Sarin et al., 1981) which measures residual free α-amino groups on the peptide-resin. Typically, coupling efficiencies of greater than 99.5% were achieved. If the coupling efficiency was unacceptable, the synthesis was repeated with a 'double coupling' cycle of the difficult residue.

Following synthesis, each peptide was individually cleaved from the resin with 10 mls anhydrous liquid HF to which was added 1 ml of dimethylsulfide, and 1 ml of a 1:0.2 molar mixture of anisole and p-thiocresol. These cleavage reactions were performed at −8° C. for 50 min. Once cleaved the resin was washed with 3–25 ml portions of anhydrous diethyl ether to remove any organic impurities that might remain. Finally, the crude peptide material was extracted from the resin with 3–10 ml washes of a dilute (30% v/v) solution of glacial acetic acid in water. The extracts were combined in a 100 ml, pear-shaped flask and the acetic acid/water solution removed by rotary evaporation. The dried-down residue that remained was brought up in a minimum volume of 0.1% TFA/$H_2O$, transferred to a 150 ml freeze-drying flask, quickly frozen in liquid nitrogen and freeze-dried overnight.

6.2. CHEMICAL CHARACTERIZATION OF SYNTHETIC PEPTIDES

The purity of the synthetic peptide was assessed first by reverse-phase HPLC, preferably using two different gradient conditions. A peptide, eluting as a single homogenous peak with greater than 95% of total area in the HPLC chromatogram, was subjected to direct amino acid sequencing for further analysis.

A. HPLC analysis

The cleaved, crude peptide material was analyzed by HPLC on a VYDAC $C_4$-analytical column (4.6 mm×250 mm) employing a gradient of 0%–60% acetonitrile over 30 min. If the gradient was inadequate, it was changed accordingly to optimize peak resolution in the crude mixture. Also, other chromatographic factors such as column sizes, packing efficiency, particle sizes, bonding chemistry of packing materials, and solubility characteristics of the peptide mixtures were considered throughout the HPLC purification process. Once an appropriate separation protocol had been obtained for each peptide, these run conditions were translated to a semi-preparative mode using a Vydac $C_4$ column (10 mm×250 mm) in order to obtain milligram to gram quantities of a purified product. Purified material was subsequently rechromatographed under analytical run conditions in order to determine the final purity of the product, an acceptable level being greater than 95%.

B. Amino acid sequence analysis

Prior to sequencing, the lyophilized peptide was dissolved in 0.1% TFA/water. Approximately 500 picomoles was spotted on a polyprene-coated glass fiber paper prior to the start of automated, repetitive Edman degradation with an Applied Biosystems 477A pulsed liquid protein/peptide sequenator equipped with an on-line Model 120A PTH-analyzer. After each Edman degradation, the phenylthiazolinone derivative formed from each amino acid was converted to the more stable phenylthiohydantoin (PTH) derivative by treatment with 25% TFA at 64° C. for 20 min.

The PTH derivatives were separated by reverse-phase HPLC over a Brownlee C-18 column (220 mm×2.1 mm) using a two solvent gradient system consisting of solvent A (per liter): 5% tetrahydrofuran containing 3M sodium acetate buffer (27.0 ml of pH 3.8 and 6.2 ml of pH 4.6) and solvent B (per liter): acetonitrile containing 500 nanomoles of oxidant scavenger, N,N-dimethyl-N-phenylthio-urea (DMPTU). To improve chromatographic peak shapes and resolution of PTH-histidine and PTH-arginine, 0.5 ml of 12.5% trimethylamine was added to solvent A. Nominal HPLC parameters were as follows: flow rate of 200 μL/min.; detector wavelength at 254 nm, and column temperature of 55° C. Optimal separation of PTH derivatives was achieved with the following linear gradient: 12% B at time 0 min., 38% B at time 18 min., 38% B at time 25 min., 90% B at time 25.1 min., 90% B at time 29 min. Each cycle's PTH was identified by comparison to a standard chromatogram of a mixture of PTH-amino acids (Applied Biosystems).

6.3. T-CELL ACTIVATION

A. Murine T-cell proliferation

Inguinal and periaortic lymph nodes were aseptically harvested from mice previously immunized with an optimal dose of antigen emulsified (1:1 vol:vol) in complete Freund's adjuvant. A single cell suspension was prepared in RPMI containing 10% fetal bovine serum. After a single washing, the cells were resuspended in RPMI without serum and counted by trypan blue exclusion with a phase contrast microscope. The cell number was adjusted to a concentration of $3 \times 10^6$ cells/ml in RPMI containing 2% normal mouse serum. Various concentrations of antigens, mitogens or other control materials were prepared in RPMI without serum and aliquoted (0.1 ml) in triplicate into 96 well, flat-bottom tissue culture treated plates. A broad range of doses was routinely employed for all antigens. To these plates, 0.1 ml of cell suspension was added. Thus, the final cell concentration achieved was $3 \times 10^5$ cells/well in media containing 1% mouse serum. After addition of the cells, the cultures were placed in a humidified, 5% $CO_2$ incubator at 37° C. Following 3 days of incubation, the cultures were pulsed for 18 hours with 1 μCi/well of [$^3$H]-thymidine and harvested for counting by liquid scintillation. Thymidine incorporation is expressed as the mean of replicate experimental values minus the mean of replicate non-stimulated (background) values.

B. Human T-cell proliferation

Blood was collected from volunteers into heparinized tubes and then diluted (1:1) with warm (37° C.) RPMI without serum. The peripheral blood leukocytes were isolated by layering the diluted blood (25 ml) over 15 ml of Ficoll histopaque (Sigma). After centrifugation (1500 rpm, 5 mins) at room temperature, the cells at the Ficoll-blood interface were aspirated and washed (3×) with RPMI containing 10% fetal bovine serum. After the final wash, the cells were resuspended in RPMI without serum and counted by trypan blue exclusion using phase contrast microscopy. The cell number was adjusted to $0.75 \times 10^6$ cells/ml in RPMI containing 20% pooled human sera. Various concentrations of antigens, mitogens or other control materials were prepared in RPMI without serum and aliquoted (0.1 ml) in triplicate into 96 wells, round-bottom tissue culture treated plates. A broad range of doses was routinely employed for all antigens. To these plates, 0.1 ml of cell suspension was added. Thus, the final cell concentration achieved was $0.75 \times 10^5$ cells/well in media containing 10% human serum. After addition of the cells, the cultures were placed in a humidified, 5% $CO_2$ incubator at 37° C. Following 6 days of incubation, the cultures were pulsed for 6–8 hours with 1 μCi/well of [$^3$H]-thymidine and harvested for counting by liquid scintillation. Thymidine incorporation is expressed as the means of replicate experimental values minus the means of replicate non-stimulated (background) values.

6.4. PREPARATION OF HbO-PEPTIDE CONJUGATES

A. Preparation of Haemophilus influenzae type b oligosaccharide (HbO)

The polysaccharide of Hib (PRP) is dissolved in water and a sufficient quantity of sodium phosphate buffer (2M, pH 7.0) is added to bring the final solution to 0.2M phosphate. Sodium metaperiodate (0.2×moles of PRP) is added all at once with rapid stirring. The solution is left in the dark at 4° C. overnight. The crude oligosaccharide is ultrafiltered on first a 30,000 MW cut-off membrane to remove the larger oligosaccharides and the filtrate ultrafiltered on a 10,000 MW cut-off membrane to remove the lower molecular weight oligosaccharides saving the retentate. The retentate is chromatographed on a BIOGEL P-100 column in saline and the fractions analyzed for ribose and reducing groups by Orcinol and Park-Johnson assays, respectively. Typically the oligosaccharides have an average Dp of 20. The purified oligosaccharide is then freeze-dried and stored at −20° C.

B. Synthesis of HbO-Peptide conjugates

The peptide is dissolved in anhydrous DMSO at a concentration of 5 mg/ml. The solution is then added to 2×mole amount of freeze-dried HbO. The amount of HbO used in the reaction can be varied from 1× to 2× depending on the type of peptide conjugate to be synthesized; double or single ended. The reaction mixture is incubated at 37° C. for 24 hrs and then 10×moles (based on HbO) of sodium borohydride dissolved in a small volume of DMSO is added. The solution is incubated for another 24 hours and then water equal to the volume of DMSO is added. The excess sodium borohydride is reacted with a small amount of acetic acid and the product is dissolved in water or saline. Unreacted peptide can be removed by size exclusion chromotography or dialysis using a 6–8,000 MW cut-off membrane. Conjugation of HbO to the peptide was verified by Western blot analysis.

6.4.1. POLYACRYLAMIDE GEL ELECTROPHORESIS (PAGE)

PRP-peptide conjugates were dissolved in 100 µl of a sample buffer (0.2M Tris buffer containing 5% SDS, 0.025% bromophenol blue, $10^{-1}$ µM 2-ME and 20% glycerol) and heated for 5 min. at 100° C. Most routine analyses were performed using the BIO-RAD Mini Protein Gel system (Redmond, Calif.). Gels were 1.5 mm thick and the separating gel contained 15% acrylamide with an acrylamide to bis ratio of 30:0.8, 0.375M Tris-HCl pH 8.8 and 0.1% SDS. The stacking gel contained 4.8% acrylamide with the same ratio of acrylamide to bis, 125 mM Tris-HCl pH 7.0 and 0.1% SDS.

Ten to fifteen microliters containing 1–10 µg of samples were applied to each lane. Following electrophoresis, gels were stained for a least 1 hour with 0.125% Coomassie blue in ethanol:acetic acid:water (5:1:5), then destained in the same solvent system without the dye. Pre-stained molecular weight standards (phosphorylase b, 92,500; bovine serum albumin, 69,000; ovalbumin, 43,000; and carbonic anhydrase 30,000) were used to assist in the determination of the relative molecular weight proteins. Duplicate gel without staining was used for Western analysis.

6.4.2. WESTERN BLOT ANALYSIS

Samples separated on PAGE were transferred electrophoretically onto nitrocellulose membranes in a Hoeffer Transphor apparatus at 0.45 mamps for 90 min. in 25 mM Tris-383 mM glycine pH 8.8 at room temperature. Once protein transfer was complete, nitrocellulose membranes were soaked in BLOTTO (5% non-fat dry milk in phosphate buffered saline) at 37° C. for 1 hour. Membranes were probed with a predetermined concentration of antibodies against PRP or $CRM_{197}$ for 1 hour at 37° C. and washed with BLOTTO for 20 min at 37° C. Bound antibodies were detected with horseradish peroxidase conjugated goat antimouse (Kirkegaard and Perry, M.D.) at 1:250 dilution in BLOTTO for 1 hour at 37° C. Blots were washed 3× with PBS and developed with PBS containing 0.01% hydrogen peroxide; 0.06% 4-chloro-1-napthol (Sigma Chemical Co., MO) in methanol for 20 min at room temperature. The reaction was stopped by transferring the filters to distilled water and the filters dried by blotting.

6.4.3. IMMUNIZATION

For the priming of murine T-cells, diphtheria toxoid, CRM or CRM peptides were dissolved in phosphate buffered saline and emulsified in an equal volume of Freund's complete adjuvant. Mice received 0.1 ml of the emulsion containing an optimal concentration of antigen subcutaneously at the base of the tail. Maximal T-cell responsiveness was routinely observed one week later.

To immunize for antibody responses, mice routinely received 2.5 µg of PRP-CRM conjugate or 5 µg of PRP-Peptide conjugates suspended in phosphate buffered saline. The conjugates were administered in a volume of 0.1 ml intramuscularly without the use of adjuvant. Any subsequent immunizations were administered at 2 week intervals using the same dose and route of injection.

6.4.4. FARR ASSAY

Antibody to PRP was determined by a standardized Farr radioimmunoassay. Various dilutions of sera, sera standard and assay controls were prepared in fetal bovine sera and 25 µl aliquots transferred, in duplicate, to 1.5 ml Eppendorf tubes. [$^3$H]-PRP (50 µl) with [$^{36}$Cl]-tracer was added to all tubes. The samples were vortexed and incubated overnight at 4° C. Saturated ammonium sulfate (75 µl) was added to all samples after which the samples were vortexed and incubated at 4° C. for 40 mins. The supernatant was carefully aspirated and 400 µl of distilled water added to all pellets. After vortexing, the entire contents of the vial and the vial itself were placed in a scintillation vial containing 10 ml of scintillation fluid. After vigorous agitation, the vials were counted on a liquid scintillation counter. The concentration of antibody bound to PRP was calculated, in comparison to a known standard, from the linear portion of plot of CPM and sera dilution.

6.4.5. ELISA ASSAY

Antibody to CRM was determined by a standard ELISA assay. To perform the assay, 96 well polystyrene plates were coated overnight at 37° C. in a humidified incubator with 100 µl/well of $CRM_{197}$ (1 µg/ml in 0.1M carbonated buffer, pH 9.6). The wells were washed (3×) with phosphate buffered saline (PBS) containing 0.05% Tween-20 and blocked with 200 µl/well PBS containing 0.1% gelatin for 45 mins at room temperature. After washing (2×) with PBS-Tween, 100 µl/well of sera diluted with diluent (PBS containing 0.05% Tween-20 and 0.1% gelatin) was added. The plates were incubated for 90 mins at room temperature and then washed (3×) with PBS-Tween. A secondary antibody (100 µl/well of 1:1000 dilution of goat-mouse alkaline phosphatase conjugate) in diluent was added and incubated for 60 mins at room temperature and washed (3×) with PBS-Tween. Substrate (100 µl/well of p-nitrophenylphosphate 1 mg/ml in diethanolamine containing $MgCl_2 \times 6H_2O$ at pH 9.8) was added and incubated for 60 mins at room temperature after which the reaction was halted by addition of 150 µl/well of 2M sodium hydroxide. Optical density at 410 and 690 nm was read using a Bio-Tek 310 Autoreader.

6.4.6. IMMUNOGLOBULIN CLASS AND SUBCLASS DETERMINATION

The class and subclass of the antibodies specific for PRP was performed in an ELISA assay. Polystyrene 96 well plates were coated with a 1/2000 dilution of PRP-tyramine in PBS. The antigen (100 µl/well) was incubated for 90 mins at 37° C. and then the plates were washed (2×) with PBS and blocked by incubation for 60 mins at room temperature with 200 µl/well of PBS containing 0.1% gelatin. After washing (2×) with PBS, 50 µl of test sera diluted in diluent (PBS containing 0.05% Tween-20 and 0.1% gelatin) was added and the plates were incubated for 2 hours at room temperature and then washed automatically with PBS containing 0.1% TWEEN-20. To the wells, 100 µl/well of an appropriate dilution of goat or rabbit anti-mouse immunoglobulin (class or subclass specific) alkaline phosphatase conjugate was added for 2 hours at room temperature. The plates were automatically washed as above. To the wells, 200 µl of substrate (p-nitrophenylphosphate, 1 mg/ml in diethanolamine containing $MgCl_2 \times 6H_2O$ at pH 9.8) was added and incubated for 60 mins at room temperature. (Depending on availability of anti-sera enzyme conjugates, however, other enzyme-substrate combinations may be employed.) The reaction was halted by addition of 50 µl/well of 2M sodium hydroxide. Optical density at 410 and 690 nm was read using a Bio-Tec 310 Autoreader.

6.5. GENERATION OF TETANUS TOXIN FRAGMENTS

The tetanus exotoxin was solubilized by heating at 100° C. for 5 min. in sample buffer containing 0.1M DTT and 2% SDS and then subjected to SDS-PAGE. Two prominent bands of protein, representing the H and L chains of the tetanus toxin, were cut from the SDS gel and extracted by electro-elution for 3 hours at 25 v in 50 mm $NH_4CO_3$, 0.2% SDS and 1 mm DTT at pH 8.2. Following electro-elution, the material was lyophilized then reconstituted immediately prior to the T-cell proliferation assay. C fragment was obtained commercially from Calbiochem, CA.

Protein fragments found to be particularly active in inducing murine T-cells were subjected to proteolytic digestion in an effort to further define T-cell epitopes. Using a digestion system composed of 0.125M Tris-HCl, 0.05M DTT, 0.5% SDS and 10% glycerol at pH 7.0, protein fragments were incubated at 37° for 30 min. with either 67 µg/ml chymotrypsin, 5 µg/ml pronase, 3 µg/ml ficin, 0.4 µg/ml subtilisin or 62.5 µg/ml v8 protease. Peptides generated in this manner can be separated by reverse phase HPLC using a Vydac C4 column. The isolated fragments can then be tested for the ability to stimulate T-cells.

6.6. RESULTS

6.6.1. PREDICTED T-CELL EPITOPES OF CRM

The DeLisi and Berzofsky algorithm (PNAS 82: 7848, 1985) for the projection of potential amphipathic regions was applied to the primary sequence of CRM as a first approximation. Computer analysis of the molecule revealed six regions within the protein, as shown in FIG. 1, which fulfilled the criteria for a possible T-cell epitope. These regions were identified as residues 1-17, 112-135, 229-256, 306-334, 357-380 and 386-408. Each of these regions is composed of a minimum of 7 consecutive residues which, when examined in the context of the primary sequence of the protein, have a tendency towards forming an alpha helical structure. In addition, region 158-173 was also arbitrarily selected to serve as a negative control material since, from computer projection, it is not expected to form an alpha helical structure. These peptides, therefore, were the focus of initial studies to delineate the T-cell epitopes within CRM.

6.6.2. ANALYSIS OF SYNTHETIC PEPTIDES

The synthetic CRM peptides with their amino acid sequences are listed in Table 1. As described above, the different sets of overlapping peptides were generated by additions to the N-terminal ends of extra amino acid residues by a solid phase approach.

Table 1 also provides the average stepwise coupling efficiency for each synthetic peptide. In all instances, the average efficiency exceeded 99%. Based on the stepwise coupling efficiency, the cumulative theoretical yields of the synthesis were also calculated; this theoretical value indicates the percent yield of the peptides having the correct amino acid sequence upon completion of the synthesis. The final column in Table 1 shows the purity of the crude peptide mixture as determined by reverse-phase HPLC analysis. A typical HPLC analysis of a crude synthesis material (peptide 6), is shown in FIG. 2A. The peptide eluted as a major peak at 25.8 mins and accounted for 66% of the total

TABLE I

CRM Synthetic Peptides

| | | CRM Peptide Sequences | Average Stepwise Coupling Efficiency (%) | Cumulative Theoretical Yield (%) | Purity (determined by HPLC) (%) |
|---|---|---|---|---|---|
| | | 307 312 317 322 327 332 337 | | | |
| CRM | Peptide 1 | I L P G I G S V M G I A D G A V H H N T E E I V A Q S I A L S S | 99.2 | 79.5 | 58.0 |
| | Peptide 2 | S V M G I A D G A V H H N T E E I V A Q S I A L S S | 99.2 | 82.1 | 47.0 |
| | Peptide 3 | A D G A V H H N T E E I V A Q S I A L S S | 99.1 | 84.7 | 71.0 |
| | Peptide 4 | H H N T E E I V A Q S I A L S S | 99.2 | 89.1 | 65.0 |
| | Peptide 5 | N T E E I V A Q S I A L S S | 99.2 | 90.7 | 68.0 |
| | | 358 363 368 373 378 383 | | | |
| CRM | Peptide 6 | A Y N F V E S I I N L F Q V V H N S Y N R P A Y S P G - G | 99.3 | 83.8 | 66.0 |
| | Peptide 7 | E S I I N L F Q V V H N S Y N R P A Y S P G - G | 99.4 | 88.4 | 66.0 |
| | Peptide 8 | N L F Q V V H N S Y N R P A Y S P G - G | 99.5 | 92.9 | 86.0 |
| | Peptide 9 | H N S Y N R P A Y S P G - G | 99.8 | 98.6 | 98.0 |
| | Peptide 10 | N S Y N R P A Y S P G - G | 99.7 | 97.1 | 100.0 |

TABLE I-continued

CRM Synthetic Peptides

| | CRM Peptide Sequences | | | | | | | | | | | | | | | | Average Stepwise Coupling Efficiency (%) | Cumulative Theoretical Yield (%) | Purity (determined by HPLC) (%) |
|---|---|---|---|---|---|---|---|---|---|---|---|---|---|---|---|---|---|---|---|
| | 368 | | | | | 373 | | | | | 378 | | | | | 383 | | | | |
| CRM Peptide 11 | L | F | Q | V | V | H | N | S | Y | N | R | P | A | Y | S | P G | 99.4 | 92.3 | 81.0 |
| Peptide 12 | | F | Q | V | V | H | N | S | Y | N | R | P | A | Y | S | P G | 99.5 | 93.3 | 78.2 |
| Peptide 13 | | | Q | V | V | H | N | S | Y | N | R | P | A | Y | S | P G | 99.5 | 94.0 | 73.0 |
| Peptide 14 | | | | V | V | H | N | S | Y | N | R | P | A | Y | S | P G | 99.5 | 94.5 | 97.0 |
| Peptide 15 | | | | | V | H | N | S | Y | N | R | P | A | Y | S | P G | 99.6 | 96.0 | 97.0 |

Figure 2B:
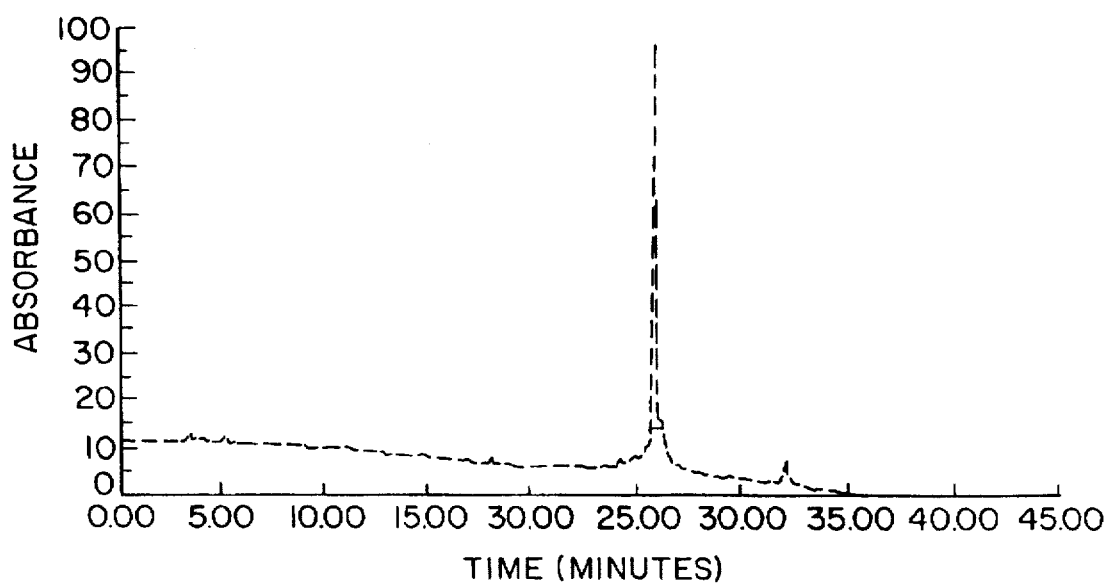
Figure 3A:
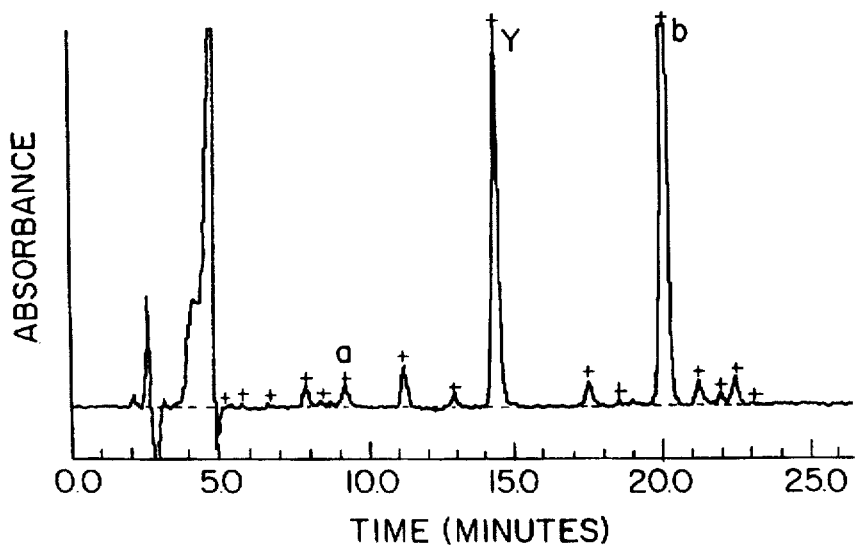
Figure 3B:
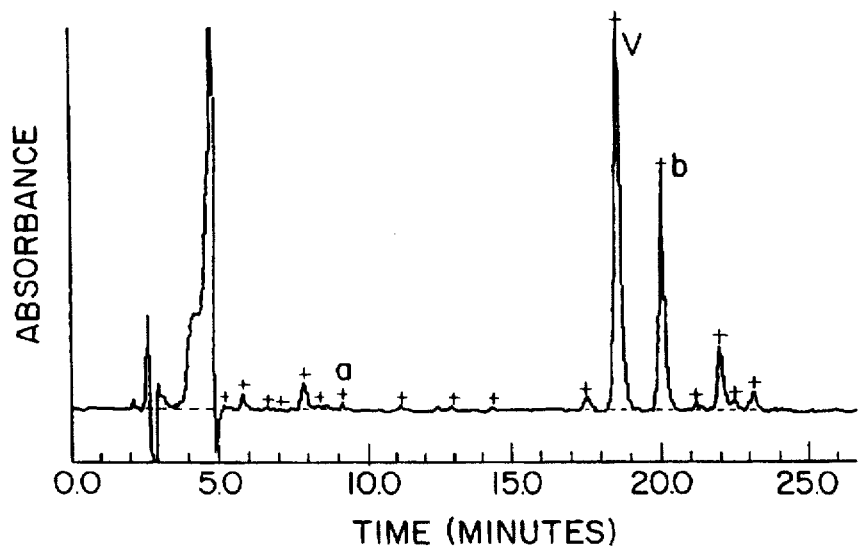
Figure 3C:
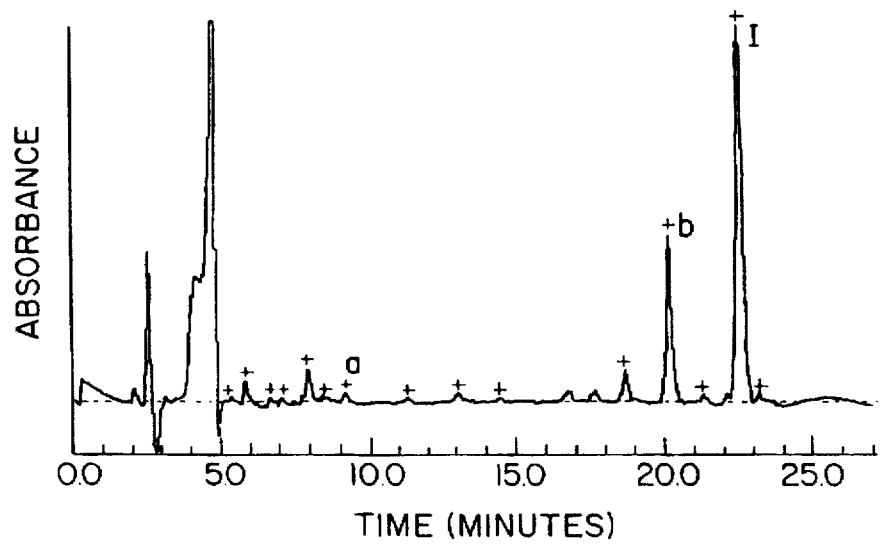
Figure 3D:
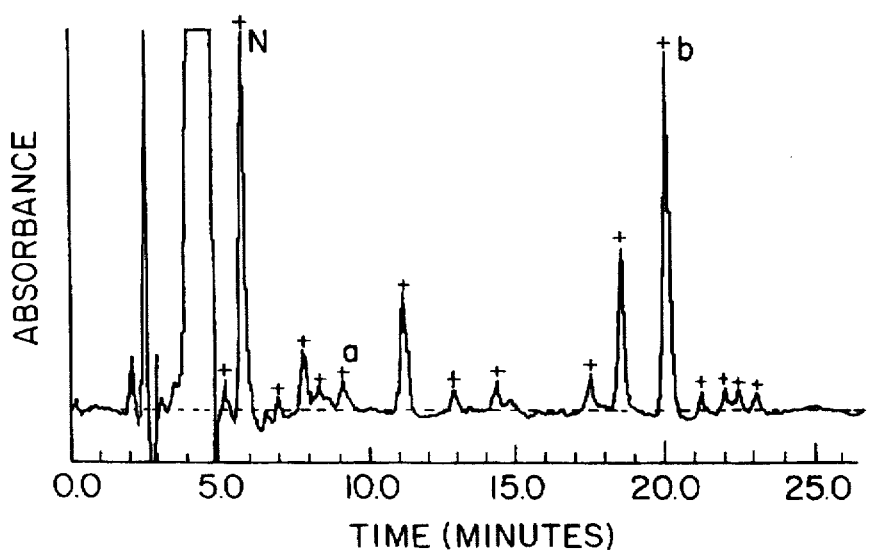
Figure 3E:
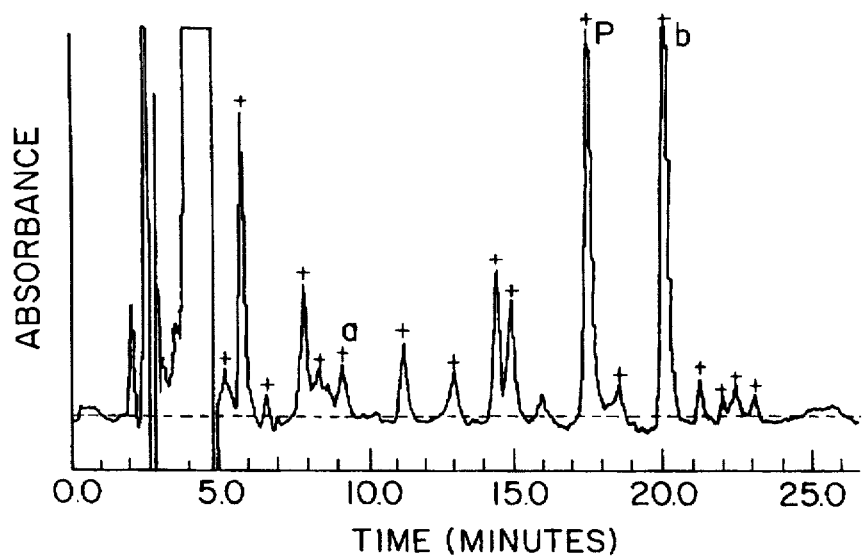
Figure 3F:
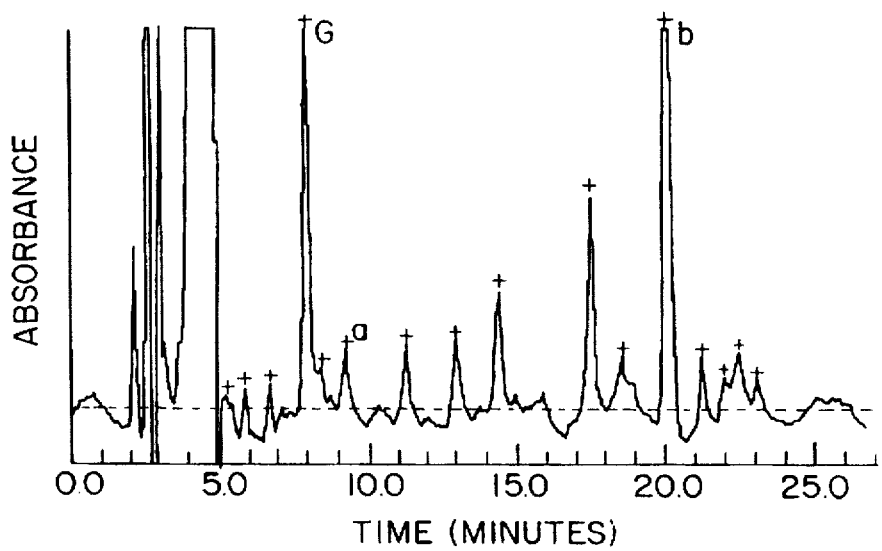

*The original epitope determinations were made with a G in the position 362 rather than an E as a result of a typographical error.

area. Fractions of this peptide material were collected, concentrated and rechromatographed as depicted in FIG. 2B. The resulting chromatogram indicated a purity of 95% or greater. In all cases crude peptide materials having less than 95% purity (Table 1) were subjected to one or more additional HPLC runs in order to obtain a final homogenous product.

The correct sequence of the synthetic peptides, as shown in Table 1, was verified by direct amino acid sequencing. As an illustrative example, FIG. 3 shows selected chromatograms of PTH-derivatives, in single letter abbreviations, from 0.5 nanomole of HPLC-purified peptide 6 spotted onto TFA-treated glass fiber disks. The numbers correspond to the Edman cycle; peaks a and b are N'N dimethyl-N'-phenylthiourea and N'N-diphenylthiourea, respectively, which are byproducts resulting from the Edman reaction. Each of the PTH chromatograms was scaled to the largest identified amino acid peak. As expected, the level of background "noise" increased at the higher cycle number; nevertheless, the amino acid peak assignment for the indicated cycles agreed with the known sequence (Table 1). Inspection of the "preview" residues (Kent et al., 1982) for each cycle also suggested the absence of deletion peptides; thus further supporting the homogeneity of the final product.

6.6.3. WESTERN BLOT ANALYSIS OF PRP-PEPTIDE CONJUGATES

Figure 4:
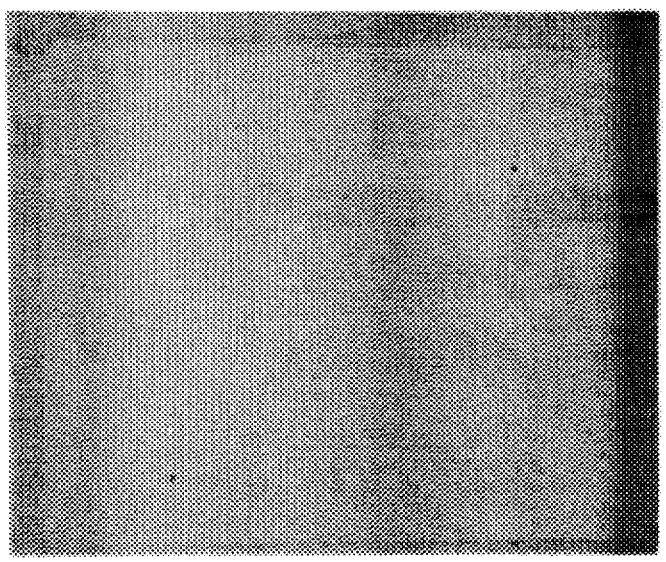

The covalent coupling of PRP to the various peptides was verified qualitatively by Western blot analysis with monoclonal antibodies specific for PRP. As shown in FIG. 4, all the peptide conjugates examined (PRP, peptide 357-380; PRP, peptide 306-334; and PRP short, peptide 366-383) were found to consist of a broad, continuous range of apparent molecular weight. Some material was retained in the stacking gel. The pattern of the peptide conjugates was very similar to that of PRP-CRM. In contrast, PRP alone, which would not be expected to be adhered to nitrocellulose upon transfer, was not detectable. Therefore, this suggests that the bands detected represent PRP covalently coupled to proteins or peptides bound to the nitrocellulose. The broad band of these conjugates may be due to glycosylation of peptides with a variety of oligosaccharide species.

6.6.4. IMMUNOGENICITY PEPTIDE PROFILE FOR MURINE T-CELL

To verify experimentally whether or not the predicted regions of CRM were, in fact, capable of inducing a T-cell proliferative response, the response of DT-primed lymph node cells to these peptides was examined. As shown in Table 2, lymph node cells obtained from DT-immune mice responded, as expected, specifically to DT and CRM, but not to TT. In addition, these cells also generated a substantial response to in vitro challenge with one of the putative T-cell epitopes, specifically region 357-380. Marginal responses to regions 306-334 and 386-408 were also observed. No response to region 158-173, the negative control peptide, or an unrelated RSV peptide was noted. In addition, the cells responded appropriately to both the T-cell mitogen,

TABLE 2

Response of Diphtheria Toxoid Primed* Murine T-Cells to the Computer Projected Amphipathic Regions of CRM

| Groups | [³H]-Thymidine Incorporation as ΔCPM + SD | In vitro Challenge Dose as µg/ml |
|---|---|---|
| Proteins | | |
| DT | 64,055 ± 4,572 | 10 |
| CRM | 51,258 ± 1,262 | 100 |
| TT | 675 ± 6 | 1 |
| Peptides | | |
| CRM(1–17) | 274 ± 28 | 50 |
| CRM(112–135) | 0 | 5 |
| CRM(158–173) | 47 ± 6 | 100 |
| CRM(229–256) | 833 ± 113 | 100 |
| CRM(306–334) | 1,100 ± 197 | 1 |
| CRM(357–380) | 12,232 ± 231 | 100 |
| CRM(386–408) | 2,478 ± 33 | 1 |
| RSV peptide | 0 | 1 |
| Mitogens | | |
| Con A | 59,092 ± 2,344 | 1 |
| LPS | 60,529 ± 5,135 | 100 |
| Background (as CPM) | 1,319 ± 269 | — |

*Mice were immunized with an optimal concentration of 50 µg DT emulsified in Freund's complete Adjuvant.
ᵇCultures were challenged with a broad range (0.05–100 µg/ml) of proteins or peptides. Only the maximal observed response is shown.

Con A, and the B-cell mitogen, lipopolysaccharide (LPS). Therefore, of the six potential T-cell epitopes identified by computer analysis, only region 357-380 was capable of stimulating a T-cell response in the murine model employed.

6.6.5. PEPTIDE ANALOGUE IMMUNOGENICITY PROFILE FOR MURINE T-CELL

To examine the possibility of alternative coupling chemistries, modified analogues of the CRM T-cell epitope 366-383 were prepared. The modifications included the addition of lysine or cysteine to the N-terminal of the peptide with or without a spacer element. The capacity of the analogues to stimulate murine T-cells was then compared with that of the non-modified peptide.

The results of T-cell stimulation assays are shown in Table 3. The study showed that the analogues of CRM peptide 366-383 retained, in comparison to 366-383 itself, most of the capacity to stimulate DT or $CRM_{197}$primed T-cells. Thus, significant changes can be made to the T-cell epitope without impairing its capacity to stimulate T-cell activity. As demonstrated, these modifications can be for the purpose of improved coupling (the example shown provides the ε-amino group for more efficient coupling), for the purpose of providing access to different coupling technologies (the example shown provides a cysteine residue), or to improve T-cell reactivity (not shown). These modifications extend the utility of peptide carriers by enabling the conjugation of a broad range of B-cell epitopes.

TABLE 3

Effects of Modification of the CRM peptide 366–383 on T-cell Recognition.

| | [$^3$H]-Thymidine incorporation (ΔCPM) | |
|---|---|---|
| Challenge | DT-primed | CRM-primed |
| Proteins | | |
| DT | 81,825 | 31,348 |
| CRM | 63,348 | 88,009 |
| TT | 804 | 0 |
| CRM Peptides | | |
| 157–173 | 1,935 | 1,147 |
| 357–383 | 23,047 | 16,009 |
| 366–383 | 43,263 | 22,722 |
| 369–383 | 40,489 | 28,198 |
| Modified CRM Peptides | | |
| L-(366–383) | 35,202 | 26,705 |
| LG-(366–383) | 33,354 | 22,852 |
| CG-(366–383) | 46,141 | 26,337 |
| RSV Peptide | 1,726 | 0 |
| Mitogens | | |
| Con A | 42,017 | 34,117 |
| LPS | 57,143 | 40,520 |
| Background | | |
| Media (as cpm) | 1,537 | 1,210 |

6.6.6. IMMUNOGENICITY PEPTIDE PROFILE FOR HUMAN T-CELL

In addition to examining the murine T-cell response to the putative T-cell epitopes, the peptide response profile or peripheral blood leukocytes from several human volunteers was examined. The individuals were selected at random and were not deliberately immunized with DT prior to assay. Therefore, the response to DT was expected to vary as a result of individual histories and upon their unique genetic composition. Two of the four individuals produced very low responses to DT or CRM and were also unresponsive to any peptide (data not shown), demonstrating that the peptides lacked any mitogenic, non-antigen specific activity. As shown in Table 4, the remaining individuals responded substantially to DT, CRM and TT and produced varying degrees of response to in vitro challenge with each of the CRM peptides. Consistent and positive responses in both individuals were noted with peptides 306-334, 357-383 and 386-408. A positive response to phytohemagglutinin (PHA), a human T-cell mitogen, was also noted.

TABLE 4

Response of Human Peripheral Blood Leukocytes to the Computer Projected Amphipathic Regions of CRM

| | [$^3$H]-Thymidine Incorporation as ΔCPM ± SD (In vitro Challenge Dose as μg/ml)* | | | |
|---|---|---|---|---|
| Groups | SP | | WM | |
| Proteins | | | | |
| DT | 244,776 ± 2,889 | (10) | 88,595 ± 8,635 | (10) |
| CRM | 186,076 ± 21,208 | (5) | 100,938 ± 12,805 | (5) |
| TT | 38,917 ± 6,911 | (5) | 143,955 ± 13,502 | (20) |
| Peptides | | | | |
| CRM(1–17) | 18,329 ± 403 | (100) | 6,932 ± 278 | (10) |
| CRM(112–135) | 10,990 ± 1,895 | (100) | 8,505 ± 214 | (10) |
| CRM(158–173) | 1,324 ± 83 | (100) | 5,346 ± 2,052 | (5) |
| CRM(229–256) | 6,803 ± 1,753 | (50) | 6,111 ± 379 | (10) |
| CRM(306–334) | 7,974 ± 1,194 | (100) | 18,023 ± 733 | (10) |
| CRM(357–380) | 10,351 ± 1,077 | (100) | 13,004 ± 881 | (100) |
| CRM(386–408) | 14,160 ± 653 | (100) | 23,337 ± 3,531 | (10) |
| RSV peptide | 0 | (5) | 5,201 ± 1,079 | (5) |
| Mitogens | | | | |
| PHA | 161,956 ± 9,267 | (5) | 37,881 ± 3,293 | (5) |
| Background (as CPM | 2,024 ± 79 | | 1,694 ± 1,778 | — |

*Cultures were challenged with a broad range (0.05–100 μg/ml) of proteins or peptides. Only the maximal observed response is shown.

6.6.7. ANTI-PEPTIDE T-CELL RESPONSES

Having demonstrated that region 357-380 of CRM was recognized by DT-primed T-cells as a T-cell epitope, it was necessary to determine whether or not the peptide itself was an effective immunogen. SJL mice, therefore, were immunized with 100 μg of CRM (357-380) or 50 μg of DT or CRM. An additional group of mice received 100 μg of CRM (306-334) as an alternative peptide to demonstrate specificity of the response. As shown in Table 5, T-cells from mice immunized with DT responded as expected to DT, CRM and peptide CRM (357-380). A similar pattern of reactivity was observed with cells from mice immunized with CRM although the responses to CRM and the peptide were substantially higher. Interestingly, CRM (357-380) primed cells responded specifically to challenge with CRM (357-380) as well as cross-reacted to the CRM protein. In contrast, CRM (306-334) primed cells did not produce a significant response to in vitro challenge with any of the proteins examined and was only weakly responsive to challenge with the immunizing peptide 306-334, itself. All of the cells, however, did respond appropriately to both Con A and LPS. Clearly, region 357-380 is not only a T-cell determinant of CRM since it is recognized by cells primed with the native protein, but it is also capable of inducing anti-peptide T-cells which can recognize the native protein.

TABLE 5

T-Cell Responses Following Peptide or Protein Priming in SJL Mice

| | [³H]-Thymidine Incorporation as ΔCPM ± SD Priming Antigens | | | |
|---|---|---|---|---|
| In Vitro Challenge | DT | CRM(306–334) | CRM(357–380) | CRM |
| Background (as CPM) | | | | |
| Media | 1,048 ± 236 | 570 ± 13 | 1,333 ± 671 | 2,058 ± 306 |
| Proteins | | | | |
| DT | 51,136 ± 4,844 | 0 | 1,857 ± 486 | 38,166 ± 3,701 |
| CRM | 48,033 ± 2,990 | 0 | 11,460 ± 924 | 144,401 ± 12,688 |
| TT | 0 | 0 | 0 | 434 ± 72 |
| Peptides | | | | |
| CRM(306–334) | 0 | 1,051 ± 183 | 0 | 0 |
| CRM(357–380) | 5,206 ± 697 | 0 | 25,140 ± 2,582 | 17,856 ± 35 |
| CRM(158–173) | 386 ± 66 | 0 | 0 | 1,335 ± 387 |
| RSV peptide | 0 | 0 | 0 | 0 |
| Mitogens | | | | |
| Con A | 66,315 ± 5,491 | 69,951 ± 2,786 | 69,762 ± 1,255 | 49,371 ± 3,564 |
| LPS | 70,018 ± 2,034 | 53,236 ± 1,633 | 55,989 ± 3,133 | 66,177 ± 1,888 |

ᵃMice were immunized with 50 μg of protein, either DT or CRM, or 100 μg of peptide, either CRM(306–337) or CRM(357–380) emulsified in Freund's complete Adjuvant.
ᵇCultures were challenged with a broad range (0.05–100 μg/ml) of proteins or peptides. Only the maximal observed response is shown.

6.6.8. REFINEMENT OF T-CELL BOUNDARIES

In order to define the minimum sequence within region 357-380 necessary to evoke a T-cell response, a set of peptides was synthesized which varied at the N-terminal. In addition, to insure that the full T-cell epitope would be within this set of peptides, the C-terminal was established at residue 384 which was four residues beyond the boundary of the active peptide, 357-380. The following peptides, therefore, were prepared and assayed for T-cell reactivity: 357-383, 362-383, 366-383, 372-383 and 373-383. As shown in Table 6, mice primed with either DT or CRM responded similarly to either peptide 357-380 or to peptide 357-383, although the response to 357-383 was slightly higher. The shorter peptide 362-383 was equivalent to 357-383 in stimulating DT-primed T-cells, but was more effective than the longer peptide in stimulating CRM-primed T-cells. Interestingly, removing four additional residues, peptide 366-383, had a dramatic effect on T-cell recognition. With both the DT and CRM primed T-cells, a greatly increased response was observed upon in vitro challenge with this peptide. Removal of additional residues, as shown with peptides 372-383 and 373-383, resulted in reduced T-cell responses in both the DT and CRM primed cells. Additionally, both groups of cells responded appropriately to DT, CRM and the mitogens.

To further define the epitope within this region, two sets of peptides were synthesized. One set of peptides consisted of a series of peptides with a C-terminal fixed at residue 383 while the N-terminal was varied stepwise from residue 357 to residue 373. The second set of peptides maintained the N-terminal at residue 366 while the C-terminal varied stepwise from residue 375 to 383. Both sets of peptides were assayed by T-cell proliferation.

TABLE 6

T-Cell Responses of Protein-Primed SJL Mice to a Nested Set of Peptides Within the Region 357–383 of CRM

| | [³H]-Thymidine Incorporation as ΔCPM ± SDᵃ (Dose as μg/ml) Priming: | | | |
|---|---|---|---|---|
| In Vitro Challenge | DT | | CRM | |
| Proteins | | | | |
| DT | 46,701 ± 1,439 | (10) | 34,027 ± 3,659 | (10) |
| CRM | 99,933 ± 2,581 | (200) | 177,440 ± 4,278 | (100) |
| PRP-CRM | 54,644 ± 885 | (100) | 126,700 ± 10,402 | (200) |
| TT | 0 | (200) | 405 ± 31 | (5) |
| Peptides | | | | |
| CRM(357–380) | 2,885 ± 89 | (50) | 10,401 ± 622 | (200) |
| CRM(357–383) | 6,637 ± 202 | (50) | 13,411 ± 451 | (50) |
| CRM(362–383) | 6,222 ± 1,432 | (0.1) | 19,673 ± 249 | (10) |
| CRM(366–383) | 32,154 ± 1,615 | (200) | 36,732 ± 580 | (50) |
| CRM(372–383) | 3,996 ± 931 | (5) | 10,661 ± 707 | (200) |
| CRM(373–383) | 876 ± 66 | (5) | 8,637 ± 1,644 | (50) |
| CRM(306–334) | 674 ± 8 | (0.1) | 4,838 ± 547 | (5) |
| CRM(158–173) | 421 ± 9 | (100) | 5,007 ± 1,016 | (200) |
| RSV Peptide | 0 | (100) | 4,557 ± 314 | (5) |
| Mitogens | | | | |
| Con A | 41,989 ± 3,206 | (1) | 48,819 ± 3,323 | (1) |
| LPS | 61,277 ± 4,477 | (50) | 59,705 ± 1,207 | (50) |
| Background (as CPM) | 1,661 ± 419 | — | 696 ± 57 | — |

ᵃMice were immunized with an optimal concentration of 50 μg DT or CRM emulsified in Freund's complete Adjuvant.
ᵇCultures were challenged with a broad range (0.1–200 μg/ml) of proteins or peptides. Only the maximal observed response is shown.

Three individual experiments were performed with similar results. A representative experiment is presented in Table 7. In mapping the N-terminal, comparable T-cell activity was seen with the inclusive peptide subset 357-383 to 370-383 in both the DT and CRM primed groups. Deletion of N-terminal residues 371, 372 or 373 resulted in pronounced decreases in T-cell activity. This observation strongly suggests that the N-terminal boundary of the T-cell epitope is residue 369 or 370. In attempting to resolve the C-terminal, the results showed that maximal T-cell activity was obtained with peptide 366-383. Any deletions of the C-terminal residues resulted in decreased T-cell activity. This finding suggests that the C-terminal of the epitope is at residue 383 or beyond. As mapped by these studies, the T-cell epitope would be localized to 369 (370)-383 of $CRM_{197}$.

TABLE 7

Mapping of N- and C-terminal boundaries of T-cell determinant within region 357–383 of CRM using lymph node cells from diphtheria toxoid or CRM-primed SJL mice.

| In Vitro | [$^3$H]-Thymidine In Vitro Incorporation as ΔCPM | |
|---|---|---|
| Challenge | DT-primed | CRM-primed |
| Proteins used as controls: | | |
| Diphtheria toxoid | 109,534 | 51,632 |
| CRM | 97,002 | 159,663 |
| Tetanus toxoid | 0 | 1,347 |
| CRM peptides used for N-terminal mapping: | | |
| CRM(357–383) | 43,577 | 41,641 |
| CRM(362–383) | 35,785 | 46,637 |
| CRM(366–383) | 57,081 | 44,403 |
| CRM(367–383) | 55,624 | 48,589 |
| CRM(368–383) | 50,543 | 63,718 |
| CRM(369–383) | 54,354 | 61,941 |
| CRM(370–383) | 73,461 | 64,320 |
| CRM(371–383) | 30,980 | 47,411 |
| CRM(372–383) | 17,460 | 24,343 |
| CRM(373–383) | 4,178 | 2,598 |
| CRM peptides used for C-terminal mapping: | | |
| CRM(366–381)-Gly | 43,429 | 39,983 |
| CRM(366–379)-Gly | 31,265 | 36,370 |
| CRM(366–377)-Gly | 15,073 | 20,023 |
| CRM(366–375)-Gly | 6,333 | 6,326 |
| CRM peptides used as controls: | | |
| CRM(158–173) | 590 | 733 |
| CRM(306–334) | 3,435 | 1,151 |
| Unrelated peptide used as control: | | |
| RSV | 0 | 1,409 |
| Mitogens: | | |
| CON A | 32,952 | 45,771 |
| LPS | 65,765 | 67,100 |
| Background (as CPM) | 2,501 | 2,007 |

6.7. ANTI-PRP AND ANTI-CRM RESPONSE ELICITED BY PEPTIDE CONJUGATES

Having preliminarily localized a determinant of T-cell recognition within CRM, it was necessary to determine whether or not the delineated region could perform as an effective carrier molecule for PRP. In addition, it was also of interest to determine whether pre-exposure to the carrier protein, DT, altered the recognition of the PRP conjugates. Accordingly, mice were immunized with DT, TT or saline emulsified in Freund's complete adjuvant. One week later, the groups of animals were immunized with a PRP conjugate. A second conjugate immunization was administered after a two week interval. The antibody response to PRP elicited in these animals is depicted in Table 8. Primary (shown at day 21) antibody responses to PRP were detected following both PRP-CRM and, significantly, PRP-(357-380), immunizations of those animals having been previously treated with DT or saline. Since antibody to PRP was evident in both of these groups, pre-exposure to DT did not apparently influence the generation of an antibody response. Rather, PRP-(357-380) was sufficient by itself to induce a primary response to PRP which was very similar in magnitude to the response elicited by PRP-CRM. Secondary responses to PRP were also detected following PRP-CRM and PRP-(357-380) immunizations. These results clearly show that a conjugate vaccine composed of PRP and synthetic peptide is capable of inducing antibodies to PRP.

TABLE 8

Antibody Response PRP-CRM Conjugate Vaccine or to PRP-CRM Peptide Conjugates in Diphtheria Toxoid Primed Mice

| IMMUNIZATION ON DAY | | | ANTIBODY TO PRP (μg/ml) AT DAY[b] | | | | |
|---|---|---|---|---|---|---|---|
| 0 | 7 | 21 | 7 | 21 | 32 | 42 | 49 |
| DT | PRP-CRM | PRP-CRM | <0.10 | 2.94 | 8.40 | 8.72 | 4.58 |
| DT | PRP-(357–383) | PRP-(357–383) | <0.10 | 3.29 | 1.39 | 6.49 | 8.43 |
| DT | PRP-(306–334) | PRP-(306–334) | <0.10 | <0.10 | 5.95 | <0.10 | <0.10 |
| DT | PRP-(229–256) | PRP-(229–256) | <0.10 | <0.10 | <0.10 | <0.10 | <0.10 |
| DT | PRP-RSV | PRP-RSV | <0.10 | <0.10 | <0.10 | <0.10 | <0.10 |
| TT | PRP-CRM | PRP-CRM | <0.10 | 0.43 | 5.02 | 4.05 | 1.03 |
| TT | PRP-(357–383) | PRP-(357–383) | <0.10 | <0.10 | 2.08 | 2.87 | 3.45 |
| TT | PRP-(306–334) | PRP-(306–334) | <0.10 | <0.10 | <0.10 | <0.10 | <0.10 |
| TT | PRP-(229–256) | PRP-(229–256) | <0.10 | <0.10 | 0.16 | <0.10 | <0.10 |
| TT | PRP-RSV | PRP-RSV | <0.10 | <0.10 | <0.10 | <0.10 | <0.10 |
| SA | PRP-CRM | PRP-CRM | 0.24 | 3.85 | 11.46 | 9.32 | 10.77 |
| SA | PRP-(357–383) | PRP-(357–383) | <0.10 | 2.32 | 3.89 | 3.85 | 4.17 |
| SA | PRP-(306–334) | PRP-(306–334) | <0.10 | <0.10 | <0.10 | <0.10 | <0.10 |
| SA | PRP-(229–256) | PRP-(229–256) | <0.10 | <0.10 | 0.31 | 0.21 | 0.29 |
| SA | PRP-RSV | PRP-RSV | <0.10 | <0.10 | 0.22 | 0.22 | 0.28 |

[a]Mice were immunized with an optimal concentration of 50 μg DT emulsified in Freund's complete adjuvant and subsequently challenged with peptide (5 μg) or protein (2.5 μg) conjugate vaccine in saline at week 1 and week 3.
[b]Sera was collected from individual mice at 7, 21, 32, 42 and 49 days after immunization with DT. Sera samples within a given group were then pooled for radioimmunoassay.

Figure 5:
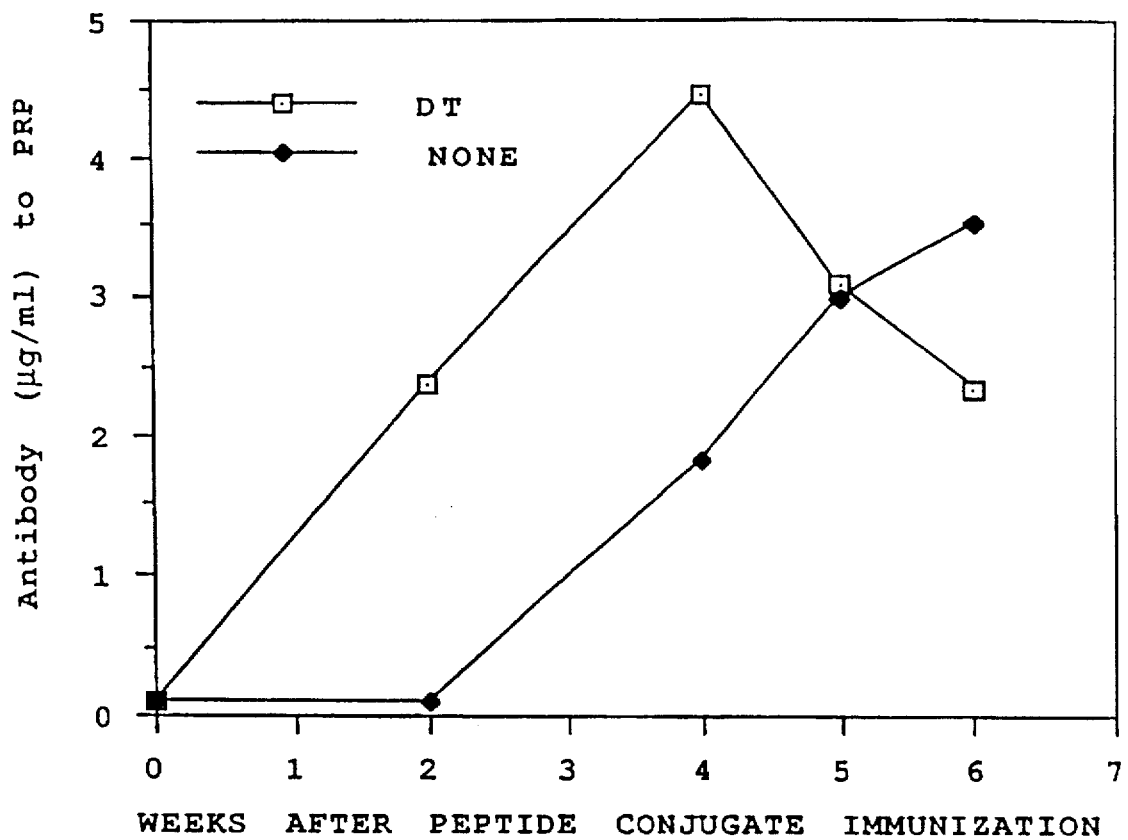
FIG. 5 shows a diagrammatic representation of the effects of pre-exposure to carrier, DT, upon the immune response to PRP-(306-334).

A secondary response to PRP was also observed following immunization with PRP-(306-334). Recall that this region was projected by computer analysis to contain a T-cell epitope, yet demonstrated minimal capacity to stimulate T-cells obtained from animals primed with diphtheria toxoid or $CRM_{197}$. In addition, this peptide was not effective in priming for an anti-peptide response. Interestingly, as shown in FIG. 5, the response following immunization with PRP-(306-334) was elicited in those animals pre-exposed to the toxoid, DT. Collectively, CRM peptide 306-334 has been demonstrated to be useful as a carrier molecule for PRP. Although standard proliferation assays have not convincingly shown this region to be a T-cell epitope, these experiments showing the positive influence of prior exposure to the intact protein support the conclusion that this region is indeed a T-cell epitope.

It is also of importance to determine if the peptide conjugates induce antibodies that cross-react with the entire CRM protein. These sera, therefore, were also screened by ELISA for anti-CRM antibodies. As shown in Table 9, binding activity to CRM was only detected in those animals immunized with PRP-CRM or pretreated with DT. None of the peptide-conjugates, when injected into the TT or saline pretreated groups, induced antibodies to CRM.

Following the procedures outlined above for PRP-CRM inoculation, mice were also immunized with conjugates of various type specific pneumococcal polysaccharides and CRM. Results of these inoculations are shown in Table 10. Again, these data show that a B-cell determinant

TABLE 9

Antibody Responses to PRP-CRM Conjugate Vaccine or to PRP-CRM Peptide Conjugates in Diphtheria Toxoid Primed Mice

| IMMUNIZATION ON DAY | | ANTIBODY TO CRM AS RECIPROCAL OF SERUM DILUTION ON DAY[b] | | | | |
|---|---|---|---|---|---|---|
| 0 | 7 | 21 | 7 | 21 | 32 | 42 | 49 |
| DT | PRP-CRM | PRP-CRM | 200 | >51,200 | >51,200 | >51,200 | >51,200 |
| DT | PRP-(357–383) | PRP-(357–383) | 400 | >51,200 | >51,200 | >51,200 | >51,200 |
| DT | PRP-(306–334) | PRP-(306–334) | 200 | >51,200 | >51,200 | >51,200 | >51,200 |
| DT | PRP-(229–256) | PRP-(229–256) | 1,600 | >51,200 | >51,200 | >51,200 | >51,200 |
| DT | PRP-RSV | PRP-RSV | 800 | >51,200 | >51,200 | >51,200 | >51,200 |
| TT | PRP-CRM | PRP-CRM | <20 | 25,600 | >51,200 | >51,200 | 25,600 |
| TT | PRP-(357–383) | PRP-(357–383) | 20 | <20 | <20 | <20 | <20 |
| TT | PRP-(306–334) | PRP-(306–334) | <20 | <20 | <20 | <20 | <20 |
| TT | PRP-(229–256) | PRP-(229–256) | <20 | <20 | <20 | <20 | <20 |
| TT | PRP-RSV | PRP-RSV | <20 | <20 | <20 | <20 | <20 |
| SA | PRP-CRM | PRP-CRM | 100 | 25,600 | >51,200 | >51,200 | >51,200 |
| SA | PRP-(357–383) | PRP-(357–383) | 20 | <20 | <20 | <20 | <20 |
| SA | PRP-(306–334) | PRP-(306–334) | <20 | 20 | 40 | 20 | 20 |
| SA | PRP-(229–256) | PRP-(229–256) | <20 | <20 | <20 | <20 | <20 |
| SA | PRP-RSV | PRP-RSV | <20 | <20 | 20 | <20 | <20 |

[a]Mice were immunized with an optimal concentration of 50 μg DT emulsified in Freund's complete adjuvant and subsequently challenged with peptide (5 μg) or protein (2.5 μg) conjugate vaccine in saline at week 1 and week 3.
[b]Sera was collected from individual mice at 7, 21, 32, 42 and 49 days after immunization with DT. Sera samples within a given group were then pooled for ELISA.

TABLE 10

Antibody Responses to Type Specific Pneumococcal Polysaccharides Administered on a Synthetic Peptide Carrier Molecule

| IMMUNIZATION | | | TYPE SPECIFIC ANTIBODY AS μg/ml AT WEEK | | | |
|---|---|---|---|---|---|---|
| Oligosacc. | Carrier | Adjuvant | 0 | 2 | 4 | 6 |
| Type 14 | Peptide | – | <0.10 | 0.19 | 2.67 | NA |
|  | Peptide | + | <0.10 | 0.41 | 3.74 | NA |
|  | CRM | – | <0.10 | 0.39 | 0.55 | NA |
| Type 19 | Peptide | – | <0.10 | <0.10 | 0.20 | NA |
|  | Peptide | + | <0.10 | <0.10 | 0.73 | NA |
|  | CRM | – | <0.10 | <0.10 | NA | NA |

Mice were immunized with type specific pneumococcal oligosaccharide coupled to $CRM_{197}$ or to the CRM peptide 357–380. Conjugate was administered at week zero and two with or without 100 μg of alum as adjuvant. Antibody values were determined by standard Farr assay.

containing antigen conjugated to a bacterial T-cell epitope can effectively elicit an immune response in the inoculated subject.

Independent confirmation of the utility of the PRP-peptide conjugate as a vaccine was obtained by functional analysis of the antibody elicited. PRP was coupled by reductive amination to the CRM peptide 369-383 which is expected to closely approximate the minimum sequence necessary to stimulate T-cells. PRP-peptide or PRP-CRM was used without adjuvant to immunize SJL mice at 0 and 2 weeks. Sera was collected as indicated in Table 11 and assayed for bactericidal activity in vitro against either of two H. influenzae strains, Eagan or the clinical isolate Hst54. A four-fold rise in titer is considered immunologically significant.

As shown in Table 11, the antibody elicited after immunization with either PRP-CRM or PRP-peptide had significant bactericidal activity against both strains as evident from the four-fold rise in titer between week 0 and 2. Further, the difference in peak achieved between the PRP-peptide and PRP-CRM immunized animals was not significantly different. The antibody elicited by the peptide conjugate is functionally equivalent to that obtained following immunization with the native protein.

6.8. ANTI-PRP AND ANTI-CRM RESPONSE ELICITED BY CONJUGATES INCLUDING A MODIFIED PEPTIDE ANALOGUE

Having determined that a modified analogue of the CRM T-cell epitope 366-383 has the capacity to stimulate

TABLE 11

Bactericidal activity of antibody elicited by immunization with PRP-peptide or PRP-CRM conjugate.

| | Bactericidal Activity at weeks Post Immunization | | |
|---|---|---|---|
| Immunogen | 0 | 2 | 4 |
| Activity against Eagan | | | |
| PRP-CRM | <1/5 | 1/20 | 1/20 |
| PRP-CRM(369–383) | <1/5 | 1/10 | 1/20 |
| Activity against Hst54 | | | |
| PRP-CRM | 1/5 | 1/80 | 1/10 |
| PRP-CRM(369–383) | <1/5 | 1/40 | 1/10 | murine T-cell proliferation, it was necessary to determine whether such an analogue can function as an effective carrier molecule. PRP was coupled by reductive amination to the lysine analogue of the CRM peptide 366-383 via the ε-amino group. After conjugation, various doses of the PRP-[Lys]-CRM(366-383) were used to immunize SJL mice without adjuvant. Animals were boosted at weeks 0 and 4. Sera was collected at the intervals shown in Table 12 and assayed for antibody specific for PRP.

As shown in Table 12, several doses of the peptide conjugate PRP-[Lys]-CRM(366-383) elicited antibody specific for PRP which exceed the 1 μg/ml concentration. The study therefore demonstrates that the lysine analogue of the CRM peptide 366-383 has utility as a carrier molecule.

TABLE 12

Initial antibody study examining the addition of an N-terminal lysine to the CRM carrier peptide 366–383 in SJL mice.

| | | Antibody (μg/ml) to PRP at weeks post immunization | | | |
|---|---|---|---|---|---|
| Immunogen | Dose | 0 | 2 | 4 | 8 |
| PRP-[Lys]-CRM(366–383) | 10 | <0.10 | <0.10 | <0.10 | <0.10 |
|  | 5 | <0.10 | 0.16 | 0.77 | 2.43 |
|  | 2.5 | 0.28 | 0.31 | 0.34 | 1.10 |
|  | 1.0 | <0.10 | 0.20 | 1.71 | 1.85 |
|  | 0.5 | <0.10 | 0.10 | 0.98 | 1.30 |

TABLE 12-continued

Initial antibody study examining the addition of an N-terminal lysine to the CRM carrier peptide 366–383 in SJL mice.

| Immunogen | Dose | Antibody (μg/ml) to PRP at weeks post immunization 0 | 2 | 4 | 8 |
|---|---|---|---|---|---|
| | 0.1 | <0.10 | 0.75 | 2.22 | 2.64 |
| PRP | 2.5 | <0.10 | <0.10 | <0.10 | 0.34 |
| PRP-CRM | 2.5 | <0.10 | 1.06 | 2.37 | 9.60 |

6.9. TETANUS TOXIN EPITOPES

Tetanus toxin H, L and C fragments were tested for their ability to stimulate murine T-cell proliferation. All three fragments induced substantial T-cell activity, however, as shown in Table 13, C fragment was clearly superior. Stimulatory activity was also observed in the human peripheral blood mononuclear cell assay. As shown in Table 14, the major T-cell activity was associated with the tetanus toxin heavy chain in this individual.

Fragment C, which was found to be very active in stimulating the proliferation of murine T-cells, was subjected to proteolytic digestion by pronase, ficin, subtilisin or V8. SDS-PAGE of the crude enzymatic digests of tetanus toxin fragment C showed no detectable intact fragment C following digestion with the four enzymes listed above. The digests were then tested for their ability to stimulate murine T-cells. Three of the protease digestion mixtures (pronase, subtilisin and V8) retained substantial T-cell activity as shown in Table 15. The data set forth in Table 15 suggests that either pronase or V8 protease digestion will yield peptide fragments particularly useful in mapping T-cell epitopes.

To further define potential T-cell epitopes within fragments generated by V8 digestion, these fragments were separated by reverse phase HPLC. Five fractions were collected and analyzed by SDS-PAGE. Four of the five fractions were found to contain major peptides and all

TABLE 13

T-cell responses of tetanus toxoid primed SJL mice to tetanus toxin fragments.

| Challenge | [$^3$H]-Incorporation (CPM) Trial #1 | Trial #2 |
|---|---|---|
| Tetanus toxoid | 50,890 | 45,284 |
| Diphtheria | 0 | 0 |
| C Fragment | 22,180 | 44,328 |
| H Chain | 18,629 | 29,870 |
| L Chain | 26,655 | 12,543 |
| Con A | 23,354 | 40,588 |
| LPS | 39,946 | 42,578 |
| Background | | |
| Media (as cpm) | 655 | 1,082 |

TABLE 14

Human proliferative responses to tetanus toxoid and tetanus toxin fragments.

| Antigen | [$^3$H]-Thymidine Incorporation ΔCPM | Dose μg/ml |
|---|---|---|
| Con A | 14,539 | — |
| PHA | 17,110 | — |
| PHA + Buffer control | 25,621 | — |
| LPS | 5,053 | — |
| Tetanus toxin | 90,271 | 10 |
| Heavy chain | 78,830 | 1 |
| Light chain | 64,290 | 100 |
| C fragment | 41,306 | 50 |
| Diphtheria toxoid | 7,973 | 100 |

TABLE 15

Enzymatic digestion of tetanus toxin C fragment - T-cell proliferative studies*.

| Enzyme | Dose (μg/ml)[a] | Treatment: | [$^3$H]-Thymidine Incorporation ΔCPM: Response to C fragment: None | Enzyme | Buffer | Enzyme Alone |
|---|---|---|---|---|---|---|
| Pronase | 1 | | 45,254 | 27,681 | 702 | 0 |
| Ficin | 0.1 | | 4,357 | 4,179 | 2,243 | 332 |
| Sub-tilisin | 1 | | 45,254 | 19,884 | 702 | 0 |
| V8 | 0.5 | | 21,903 | 30,264 | 8,187 | 0 |

*Control responses as ΔCPM (dose at maximal response): TT 102,730 (5); C fragment 120,126 (100); DT 397 (0.5); Con A 31,343 (1) and LPS 39,750 (50). The background response was 1,334 cpm.
[a]Dose of fragment C in enzymatic digest. 'None' refers to the response to fragment C alone at the dose where a maximum response was obtained in the digest.

were tested in the murine T-cell proliferation assay. As shown in Table 16, fractions 3, 4 and 5 induced a significant T-cell response. Fraction 3 contains a major band having a molecular weight of 10K and fractions 4 and 5 contain major bands of approximately 22K and 17K, respectively.

To further analyze the V8 digestion fragments, fractions 1–5 were separated by SDS-PAGE, transferred to Immobilon paper (Millipore) and directly sequenced. Partial sequences of two fragments, the 22K from fraction 4 and the 17K band from fraction 5, have been determined and compared to the known sequence of tetanus toxin (Eisel et al., *EMBO J.* 5: 2495–2502, 1986). Based upon molecular weight estimates from SDS-PAGE and sequencing data, it was concluded that the 22K fragment corresponds to tetanus toxin residues 1128-1309 and the 17K fragment from residues 974-1116.

In order to more closely localize the T cell epitopes within the C fragment, the strategy of using overlapping synthetic peptides was used. This strategy required the synthesis of 37 peptides of 19–20 residues in length and with a seven residue overlap to examine the entire primary sequence of the C fragment. Since the protease digestion studies suggested that T cell activity was potentially associated with the 17K and the 22K fragments, the initial effort was focused on the most potent of these two regions. As shown in Table 17, overlapping synthetic peptides beginning at residue 97 and spanning a portion of the region 974-1116 were examined for T cell activity. Of those examined, tetanus toxin peptide 961-980 and 1021-1040 which fall within the C fragment provoked significant T-cell proliferative responses by tetanus toxoid-primed murine lymphocytes. Thus, two potential T cell epitopes of tetanus toxin fragment C have been localized by the application of these techniques.

TABLE 16

Proliferative response of tetanus toxoid primed T-cells to fragment C and peptides of fragment C.

| | Max CPM ± SD (dose µg/ml) |
|---|---|
| Media | 945 ± 234 |
| CA 1.0 µg/ml | 37,758 ± 687 |
| LPS 50.0 µg/ml | 61,390 ± 2,662 |
| Tet. toxoid | 149,578 ± 10,581 |
| Dipth. toxoid | 879 ± 26 |
| C fragment | 140,025 ± 10,156 |
| Protease frac. 1 | 1,270 ± 8 |
| Protease frac. 2 | 1,828 ± 240 |
| Protease frac. 3 | 5,158 ± 372 |
| Protease frac. 4 | 14,772 ± 1,308 |
| Protease frac. 5 | 23,065 ± 1,181 |

TABLE 17

T cell responses of Tetanus toxoid-primed lymph node cells to overlapping synthetic peptides comprising a selected region of tetanus fragment C.

| In Vitro Challenge | [$^3$H]-thymidine Incorporation (ΔCPM) | Dose (µg/ml) |
|---|---|---|
| Proteins | | |
| Tetanus toxoid | 242,421 | 5 |
| Tetanus Fragment C | 296,801 | 100 |
| Diptheria toxoid | 3,892 | 1 |
| Tetanus toxin peptides | | |
| 961–980 | 32,276 | 100 |
| 973–992 | 10,457 | 100 |
| 997–1016 | 6,347 | 100 |
| 985–1004 | 3,600 | 50 |
| 1009–1028 | 5,130 | 100 |
| 1021–1040 | 100,332 | 50 |
| 1273–1292 | 11,230 | 50 |
| Mitogens | | |
| Con A | 44,077 | 1 |
| LPS | 86,740 | 50 |
| Background | | |
| Media (as cpm) | 3,639 | |

7.0 ANTIBODY RESPONSE TO NON-CARBOHYDRATE HAPTEN CONJUGATES

Figure 6:
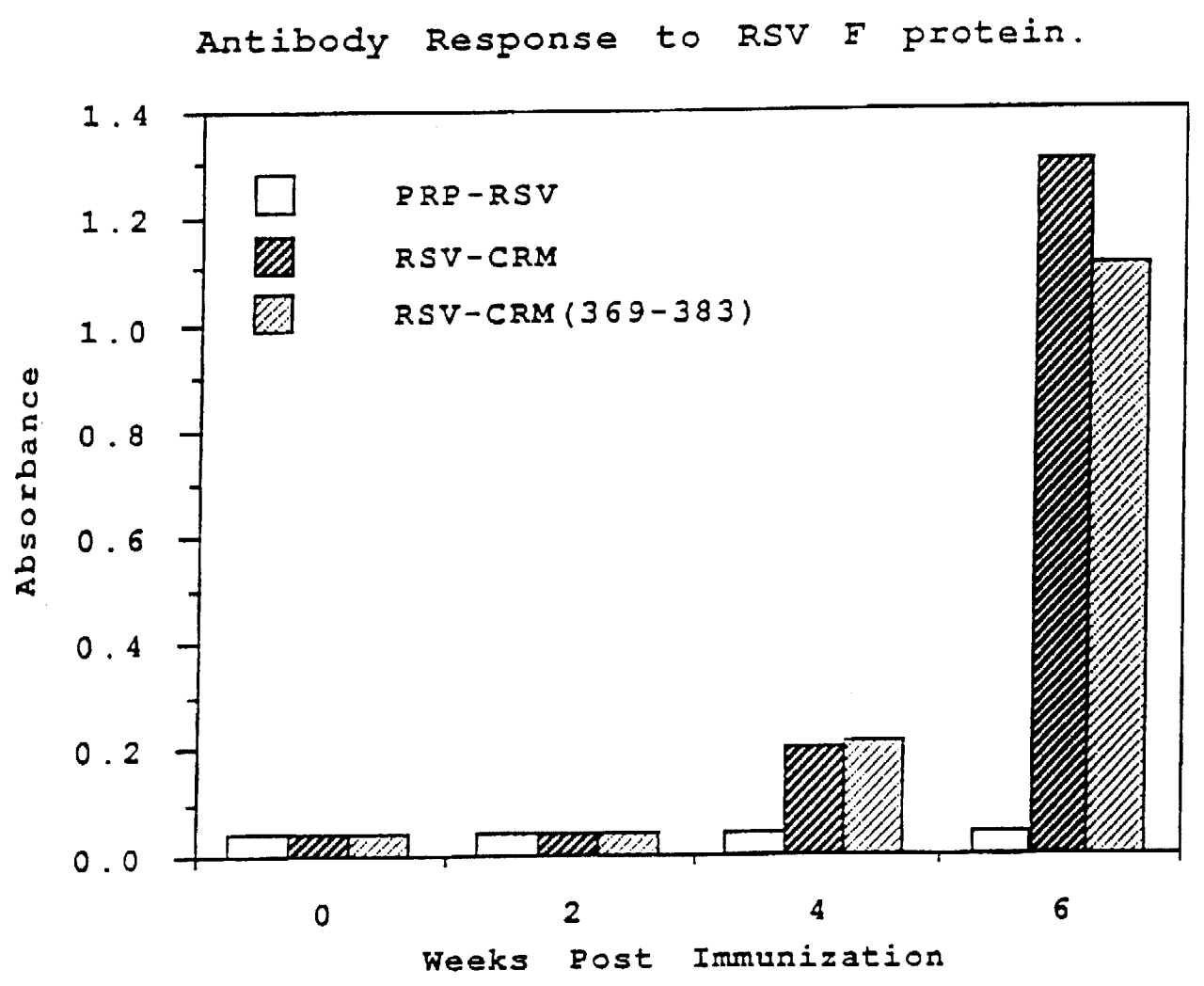

The B-cell epitope of the Respiratory Syncytial Virus (RSV) protein F was coupled to the CRM T-cell epitope 369-383 or to the intact native protein. SJL mice were immunized at weeks 0 and 2 with 5 µg weight equivalent of peptides 369-383 mixed with alum. Sera were collected. As shown in FIG. 6, antibody to the RSV F protein was elicited following immunization with the B-cell epitope of RSV (283-315) coupled to either whole CRM or to the CRM peptide 369-383. This experiment demonstrates the utility of the CRM peptide 369-383 to serve as a carrier molecule for materials other than carbohydates. In this case, the specific example is a peptide representing a B-cell epitope of a viral protein.

What is claimed is:

1. An immunogenic conjugate consisting of a polysaccharide antigen covalently bound to one T-cell epitope of tetanus toxin, diphtheria toxin or pertussis.

2. The conjugate of claim 1, wherein the diphtheria toxin is $CRM_{197}$.

3. An immunogenic conjugate consisting of a polysaccharide antigen covalently bound to a T-cell epitope which is amino acid residues 357-383 of $CRM_{197}$, or a variation thereof consisting of the addition of a lysine or a cysteine, with or without a glycine spacer element, to the amino terminus of the T-cell epitope, which epitope retains the ability to stimulate T cells.

4. An immunogenic conjugate consisting of a polysaccharide antigen covalently bound to a T-cell epitope which is amino acid residues 366-383 of $CRM_{197}$, or a variation thereof consisting of the addition of a lysine or a cysteine, with or without a glycine spacer element, to the amino terminus of the T-cell epitope, which epitope retains the ability to stimulate T cells.

5. An immunogenic conjugate consisting of a polysaccharide antigen covalently bound to a T-cell epitope which is amino acid residues 369-383 of $CRM_{197}$, or a variation thereof consisting of the addition of a lysine or a cysteine, with or without a glycine spacer element, to the amino terminus of the T-cell epitope, which epitope retains the ability to stimulate T cells.

6. An immunogenic conjugate consisting of a polysaccharide antigen covalently bound to a T-cell epitope which is amino acid residues 306-334 of $CRM_{197}$, or a variation thereof consisting of the addition of a lysine or a cysteine, with or without a glycine spacer element, to the amino terminus of the T-cell epitope, which epitope retains the ability to stimulate T cells.

7. The conjugate of claim 1, wherein the toxin is tetanus toxin.

8. An immunogenic conjugate consisting of a polysaccharide antigen covalently bound to a T-cell epitope which is amino acid residues 961-980 of tetanus toxin, or a variation thereof consisting of the addition of a lysine or a cysteine, with or without a glycine spacer element, to the amino terminus of the T-cell epitope, which epitope retains the ability to stimulate T cells.

9. An immunogenic conjugate consisting of a polysaccharide antigen covalently bound to a T-cell epitope which is amino acid residues 1021-1040 of tetanus toxin, or a variation thereof consisting of the addition of a lysine or a cysteine, with or without a glycine spacer element, to the amino terminus of the T-cell epitope, which epitope retains the ability to stimulate T cells.

10. The conjugate of claim 1, wherein the polysaccharide antigen is selected from the group consisting of microbial antigens, viral antigens, parasitic antigens, tumor antigens and allergens.

11. The conjugate of claim 1, wherein the polysaccharide antigen is derived from Haemophilus influenzae, Streptococcus pneumoniac, Neisseria meningitidis, Streptococcus aureus or Streptococcus agalactiae.

12. The conjugate of claim 11, wherein the polysaccharide antigen is polyribosylribitolphosphate of H. influenzae.

13. The conjugate of claim 11, wherein the polysaccharide antigen is derived from Streptococcus pneumoniae.

14. The conjugate of claim 13, wherein the polymer is from serotype 1, 4, 5, 6A, 6B, 9V, 14, 18C, 19F or 23F of S. pneumoniae.

15. The conjugate of claim 10, wherein the polysaccharide antigen is a bacterial surface or cell wall saccharide.

16. The conjugate of claim 15, wherein the polysaccharide antigen is lipopolysaccharide of gram negative bacteria.

17. An immunogenic conjugate consisting of a polysaccharide antigen covalently bound to a T-cell epitope having the amino acid sequence QVVHNSYNRPAYSPG.

18. The immunogenic conjugate of claim 17, wherein the polysaccharide antigen is bound to the T-cell epitope through a lysine or cysteine residue coupled to an amino terminus of the said T-cell epitope.

19. The immunogenic conjugate of claim 18, wherein the lysine or cysteine residue is coupled to the T-cell epitope amino terminus through a glycine residue.

20. An immunogenic conjugate consisting of a polysaccharide antigen covalently bound to a T-cell epitope having the amino acid sequence NLFQVVHNSYNRPAYSPG, AYNFVE (or G) SIINLFQVVHNSYNRPAYSPG or ILPGIGSVMGIADGAVHHNTEEIVAQSIA.

21. The immunogenic conjugate of claim 20, wherein the polysaccharide antigen is bound to the T-cell epitope through a lysine of cysteine residue coupled to the amino terminus of the T-cell epitope.

22. The immunogenic conjugate of claim 21, wherein the lysine or cysteine residue is coupled to the T-cell epitope amino terminus through a glycine residue.

23. An immunogenic conjugate consisting of a polysaccharide antigen covalently bound to a T-cell epitope having the amino acid sequence VSASHLEQYGTNEYSIISSM or DKFNAYLANKWVFITITNDR.

24. The immunogenic conjugate of claim 23, wherein the polysaccharide antigen is bound to the T-cell epitope through a lysine or cysteine residue coupled to the oligopeptide amino terminus of the T-cell epitope.

25. The immunogenic conjugate of claim 24, wherein the lysine or cysteine residue is coupled to the T-cell epitope amino terminus through a glycine residue.

26. An immunoconjugate consisting of polyribosylribitolphosphate covalently bound to a T-cell epitope having the amino acid sequence of the peptide 369-383 of $CRM_{197}$.

* * * * *